(12) United States Patent
Orme et al.

(10) Patent No.: US 7,105,506 B2
(45) Date of Patent: Sep. 12, 2006

(54) TETRACYCLIC COMPOUNDS AS PDE5-INHIBITORS

(75) Inventors: Mark W. Orme, Seattle, WA (US); Jason S. Sawyer, Indianapolis, IN (US); Lisa M. Schultze, Woodinville, WA (US)

(73) Assignee: Lilly Icos LLC, Wilmington, DE (US)

( * ) Notice: Subject to any disclaimer, the term of this patent is extended or adjusted under 35 U.S.C. 154(b) by 336 days.

(21) Appl. No.: 10/479,352

(22) PCT Filed: May 2, 2002

(86) PCT No.: PCT/US02/13703

§ 371 (c)(1),
(2), (4) Date: Nov. 25, 2003

(87) PCT Pub. No.: WO02/098428

PCT Pub. Date: Dec. 12, 2002

(65) Prior Publication Data

US 2004/0162291 A1 Aug. 19, 2004

Related U.S. Application Data

(60) Provisional application No. 60/296,041, filed on Jun. 5, 2001.

(51) Int. Cl.
*A01N 43/00* (2006.01)
*A01N 43/62* (2006.01)
*A01N 43/66* (2006.01)
*A61K 31/553* (2006.01)
*A61K 31/55* (2006.01)

(52) U.S. Cl. ............ 514/211.1; 514/219; 514/249; 540/546; 540/555; 540/578; 544/246

(58) Field of Classification Search ............ None
See application file for complete search history.

(56) References Cited

U.S. PATENT DOCUMENTS 5,859,006 A 1/1999 Daugan 5,981,527 A * 11/1999 Daugan et al. ............ 514/250
6,046,199 A * 4/2000 Pamukcu et al. .......... 514/250

FOREIGN PATENT DOCUMENTS

DE 100 21 266 11/2000

OTHER PUBLICATIONS

Fantauzzi and Yager "Synthesis of Diverse Tetrahydro-β-Carboline-3-Carboxamides and -2,3-Bis-lactams On a Versatile 4-Hydroxythiophenol-Linked Solid Support" Tetrahedron Letters, vol. 39, pp. 1291-1294 (1998).*
Wang and Ganesan "The N-Acyliminium Pictet-Spengler Condensation as a Multicomponent Combinatorial Reaction on Solid Phase and Its Application to the Synthesis of Demethoxyfumitremorgin C Analogues" Organic Letters, vol. 1(10), pp. 1647-1649 (1999).*
Wang et al, "Synthesis and Evaluation of Tryprostatin B and Demethoxyfumitremorgin C Analogues" Journal of Medicinal Chemistry, vol. 43, pp. 1577-1585 (2000).*

* cited by examiner

*Primary Examiner*—James O. Wilson
*Assistant Examiner*—Zachary Tucker
(74) *Attorney, Agent, or Firm*—Marshall, Gerstein & Borun LLP

(57) ABSTRACT

Compounds of structural formula (I) and use of the compounds and salts and solvates thereof, as therapeutic agents.

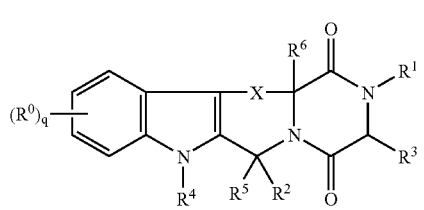

26 Claims, No Drawings

TETRACYCLIC COMPOUNDS AS PDE5-INHIBITORS

CROSS-REFERENCE TO RELATED APPLICATIONS

This is the U.S. national phase application of International Application No. PCT/US02/13703, filed May 2, 2002, which claims the benefit of U.S. provisional patent application Ser. No. 60/296,041, filed Jun. 5, 2001.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3′,5′-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

SUMMARY OF THE INVENTION

The present invention provides compounds of formula (I)

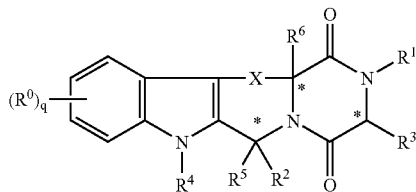

wherein $R^0$ is selected from the group consisting of halo and $C_{1-6}$alkyl;

$R^1$ is selected from the group consisting of hydro, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl-$C_{1-3}$alkyl, and heteroaryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

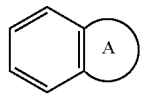

wherein the fused ring A is a 5- or 6-membered ring, saturated or partially or fully unsaturated, and comprises carbon atoms and optionally one or two heteroatoms selected from oxygen, sulfur, and nitrogen;

$R^3$ is selected from the group consisting of hydro and $C_{1-3}$alkyl, or $R^1$ and $R^3$ together represent a 3- or 4-membered alkyl or alkenyl chain component of a 5- or 6-membered ring;

$R^4$ is selected from the group consisting of hydro, $C_{1-6}$alkyl, $C_{3-8}$cycloalkyl, $C_{3-8}$-heterocycloalkyl, $C_{2-6}$alkenyl, $C_{1-3}$alkylenearyl, aryl$C_{1-3}$alkyl, $C(=O)R^a$, aryl, heteroaryl, $C(=O)R^a$, $C(=O)NR^aR^b$, $C(=S)NR^aR^b$, $SO_2R^a$, $SO_2NR^aR^b$, $S(=O)R^a$, $S(=O)NR^aR^b$, $C(=O)NR^aC_{1-4}$-alkyleneOR$^a$, $C(=O)NR^aC_{1-4}$alkyleneHet, $C(=O)C_{1-4}$alkylenearyl, $C(=O)C_{1-4}$alkyleneheteroaryl, $C_{1-4}$alkylenearyl substituted with one or more of $SO_2NR^aR^b$, $NR^aR^b$, $C(=O)OR^a$, $NR^aSO_2CF_3$, CN, $NO_2$, $C(=O)R^a$, $OR^a$, $C_{1-4}$alkyleneNR$^aR^b$, and $OC_{1-4}$alkyleneNR$^aR^b$, $C_{1-4}$alkyleneheteroaryl, $C_{1-4}$alkyleneHet, $C_{1-4}$alkyleneC(=O)$C_{1-4}$alkylenearyl, $C_{1-4}$alkyleneC(=O)$C_{1-4}$alkyleneheteroaryl, $C_{1-4}$-alkyleneC(=O)Het, $C_{1-4}$alkyleneC(=O)NR$^aR^b$, $C_{1-4}$alkyleneOR$^a$, $C_{1-4}$alkyleneNR$^aC(=O)R^a$, $C_{1-4}$alkyleneOC$_{1-4}$alkyleneOR$^a$, $C_{1-4}$alkyleneNR$^aR^b$, $C_{1-4}$alkyleneC(=O)OR$^a$, and $C_{1-4}$alkyleneOC$_{1-4}$alkyleneC(=O)OR$^a$;

$R^5$ is selected from the group consisting of hydro, $OR^a$, $C_{1-6}$alkyl, aryl, heteroaryl, aryl$C_{1-3}$alkyl, $C_{1-3}$alkylenearyl, $C_{1-3}$alkyleneHet, $C_{3-8}$cycloalkyl, and $C_{3-8}$heterocycloalkyl;

$R^6$ is selected from the group consisting of hydro, $C_{1-6}$alkyl, $C_{3-8}$cycloalkyl, $C_{3-8}$heterocycloalkyl, aryl, heteroaryl, $OR^a$, $C(=O)OR^a$, $C(=O)R^a$, $C(=O)NR^aR^b$, $C(=S)OR^a$, and $C(=S)NR^aR^b$;

X is selected from the group consisting of CHR$^7$, CHR$^7$CH$_2$, CH$_2$CHR$^7$, CR$^7$=CH, CH=CR$^7$, QCHR$^7$, and CHR$^7$Q, or X is a bond;

Q is O, S, or NR$^a$;

$R^7$ is selected from the group consisting of hydro, $OR^a$, $C_{1-6}$alkyl, $C_{3-8}$cycloalkyl, $C_{3-8}$heterocycloalkyl, aryl, heteroaryl, $C_{1-3}$alkylenearyl, $C_{1-3}$alkyleneheteroaryl, $C_{1-3}$alkyleneHet, aryl$C_{1-3}$alkyl, and heteroaryl$C_{1-3}$alkyl;

Het represents a 5- or 6-membered heterocyclic ring saturated or partially or fully unsaturated, containing at least one heteroatom selected from the group consisting of oxygen, nitrogen, and sulfur, and optionally substituted with $C_{1-4}$alkyl or $C(=O)OR^a$;

$R^a$ is selected from the group consisting of hydro, $C_{1-6}$alkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

$R^b$ is selected from the group consisting of hydro, $C_{1-6}$alkyl, aryl, heteroaryl, aryl$C_{1-3}$alkyl, heteroaryl$C_{1-3}$ alkyl, $C_{1-3}$alkyleneN(R$^a$)$_2$, $C_{1-3}$alkylenearyl, $C_{1-3}$alkyleneHet, halo$C_{1-3}$alkyl, $C_{3-8}$cycloalkyl, $C_{3-8}$heterocycloalkyl, $C_{1-3}$alkyleneheteroaryl, $C_{1-3}$-alkyleneC(=O)OR$^a$, and $C_{1-3}$alkyleneC$_{3-8}$heterocycloalkyl;

or $R^a$ and $R^b$ are taken together to form a 5- or 6-membered ring, optionally containing at least one heteroatom;

q is 0, 1, 2, 3, or 4;

with the proviso that if X is CHR$^7$, at least one of $R^4$, $R^5$, $R^6$, and $R^7$ is different from hydro; and pharmaceutically acceptable salts and hydrates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic $C_3$–$C_8$ hydrocarbon group, e.g., cyclopropyl, cyclobutyl, cyclohexyl, and cyclopentyl.

The terms "alkenyl" and "alkynyl" are defined identically as "alkyl," except for containing a carbon-carbon double bond or carbon-carbon triple bond, respectively. "Cycloalkenyl" is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" is defined as monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl" is defined as —CF$_3$.

The term "trifluoromethoxy" is defined as —OCF$_3$.

The term "cyano" is defined as —CN.

In a preferred embodiment, q is 0.

In preferred embodiments, R$^1$ is selected from the group consisting of $C_{1-6}$alkyl, $C_{3-8}$cycloalkyl, $C_{2-6}$alkenyl, and halo$C_{1-6}$alkyl.

In a preferred embodiments, R$^2$ is an optionally substituted bicyclic ring system

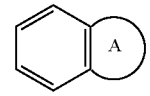

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

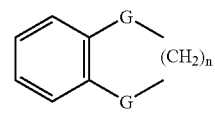

wherein n is an integer 1 or 2, and G, independently, is C(R$^a$)$_2$, O, S, or NR$^a$. The bicyclic ring comprising the R$^2$ substituent typically is attached to the rest of the molecule by a phenyl ring carbon atom.

In another preferred group of compounds of formula (I), R$^2$ is represented by an optionally substituted bicyclic ring

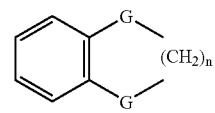

wherein n is 1 or 2, and G, independently, are CH$_2$ or O. Especially preferred R$^2$ substituents include

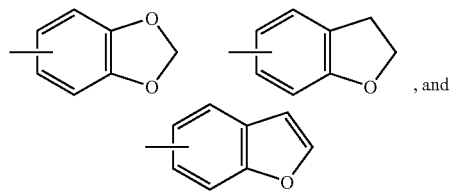

Within this particular group of compounds, nonlimiting examples of substituents for the bicyclic ring include halo (e.g., chloro), $C_{1-3}$alkyl (e.g., methyl, ethyl, or i-propyl), OR$^a$ (e.g., methoxy, ethoxy, or hydroxy), CO$_2$R$^a$, halomethyl or halomethoxy (e.g., trifluoromethyl or trifluoromethoxy), cyano, nitro, and NR$^a$R$^b$.

In a preferred embodiment, R$^4$ is selected from the group consisting of hydro, aryl, heteroaryl, $C_{1-4}$alkyleneHet, $C_{1-4}$alkyleneheteroaryl, $C_{1-4}$alkylenearyl, $C_{1-4}$alkyleneC(=O)$C_{1-4}$alkylenearyl, $C_{1-4}$alkyleneC(=O)OR$^a$, $C_{1-4}$alkyleneC(=O)NR$^a$R$^b$, C$_{1-4}$-alkyleneC(=O) Het, C$_{1-4}$alkyleneNR$^a$R$^b$, C$_{1-4}$alkyleneNR$^a$C(=O)R$^a$, and C$_{1-4}$alkyleneOC$_{1-4}$alkyleneOR$^a$.

In more preferred embodiments, R$^4$ is selected from the group consisting of hydrogen; C$_{1-4}$alkyleneheteroaryl, wherein the heteroaryl group is selected from the group consisting of benzimidazole, a triazole, and imidazole; C$_{1-4}$alkyleneHet, wherein Het is selected from the group consisting of piperazinyl, morpholinyl, pyrrolidinyl, pyrrolidonyl, tetrahydrofuranyl, piperidinyl,

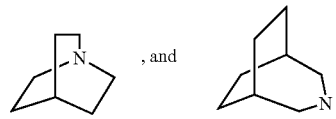

and C$_{1-4}$alkyleneC$_6$H$_5$, optionally substituted with one to three groups selected from the group consisting of C(=O)OR$^a$, NR$^a$R$^b$, NR$^a$SO$_2$CF$_3$, SO$_2$NR$^a$R$^b$, CN, OR$^a$, C(=O)R$^a$, C$_{1-4}$alkyleneNR$^a$R$^b$, nitro, OC$_{1-4}$alkylenearyl, and OC$_{1-4}$ alkyleneNR$^a$R$^b$; C$_{1-4}$alkyleneC(=O)benzyl; C$_{1-4}$alkyleneC(=O)OR$^a$; C$_{1-4}$alkyleneC(=O)NR$^a$R$^b$; C$_{1-4}$alkyleneC(=O)-NR$^a$R$^c$; OC$_{1-4}$alkyl; C$_6$H$_5$; C$_{1-4}$alkyleneNR$^a$R$^b$; C$_{1-4}$alkylene-OR$^a$; C$_{1-4}$alkyleneNHC(=O)R$^a$; and C$_{1-4}$alkyleneOC$_{1-4}$alkyleneOR$^a$.

In preferred embodiments, R$^5$ is selected from the group consisting of hydro, OR$^a$, C$_{1-6}$alkyl, aryl, and heteroaryl.

In preferred embodiments, R$^6$ is selected from the group consisting of hydro, C$_{1-6}$alkyl, C$_{3-8}$cycloalkyl, C$_{3-8}$heterocycloalkyl, OR$^a$, aryl, and heteroaryl.

In preferred embodiments, X is a bond, or X is selected from the group consisting of CHR$^7$, CHR$^7$CH$_2$, CH$_2$CHR$^7$, CH=CR$^a$, and CR$^a$=CH; and R$^7$ is selected from the group consisting of hydro, OR$^a$, C$_{1-6}$alkyl, aryl, heteroaryl, C$_{3-8}$cycloalkyl, and C$_{3-8}$heterocycloalkyl.

In especially preferred embodiments, q is 0, or R$^0$ is selected from the group consisting of halo and methyl; R$^1$ is methyl; R$^2$ is selected from the group consisting of

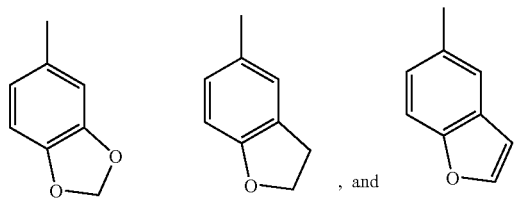

R$^4$ is selected from the group consisting of hydrogen and C$_{1-6}$alkyl; R$^5$ is selected from the group consisting of H, CH$_3$, and OH; R$^6$ selected from the group consisting of hydro, methyl, OH, phenyl, and cyclohexyl; and X is selected from the group consisting of CHR$^7$ and CHR$^7$CH$_2$, or X is a bond; and R$^7$ is selected from the group consisting of hydrogen, OH, methyl, and phenyl.

An especially preferred subclass of compounds within the general scope of formula (I) is represented by compounds of formula (II)

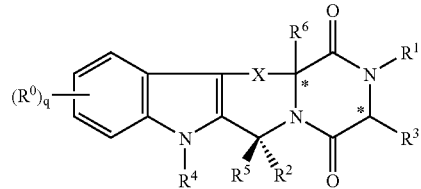

(II)

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable.

The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient.

The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogen-, free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, $R^3$, $R^4$, $R^5$, $R^6$, and $R^7$, as well as X, are defined as in structural formula (I) above. In particular, compounds of structural formula (I) can be prepared according to the following synthetic schemes.

Daugan U.S. Pat. No. 5,859,006, incorporated herein by reference, discloses preparation of a compound of structural formula (III):

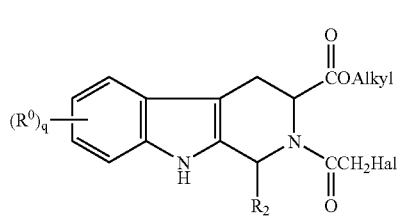

The compounds of structural formula (I) can be prepared in an analogous manner as a compound of structural formula (III) using appropriately substituted starting materials.

In the following Method A, the 1,2,3,4-tetrahydro-β-carboline (IV) is prepared from Compound (III) by the Pictet-Spengler reaction. See A. Madrigal et al., *Org. Chem.*, 63, p. 2724 (1998); P. D. Bailey et al., *Tetrahedron Lett.*, 35, p. 3587 (1994); K. M. Czerwinski et al., Stereochemical Control of the Pictet-Spengler Reaction in the Synthesis of Natural Products, in *Adv. Heterocycl. Nat. Prod. Synth.*, 3, p. 217 (1996), W. H. Pearson Ed., JAI Press, Greenwich; P. D. Bailey et al., *J. Chem. Soc., Perkin Trans.* 1, pp. 431–439 (1993); and E. D. Cox et al., *Chem. Rev.*, 95, p. 1797 (1995).

In particular, the substituted tryptophan ester (III) is reacted with either an aldehyde, ketone, or equivalent to give Compound (IV). See, R. S. Hoerner et al., *Tetrahedron Lett.*, 39, p. 3455 (1998); L. Jeannin et al., *Tetrahedron Lett.*, 36, p. 2057 (1995); L. W. Boteju et al., *Tetrahedron Lett.*, 33, p. 7491 (1992); and T. Nagy et al., *Eur. J. Med. Chem.*, 30, p. 575 (1995). Compound (IV) then is treated with either an amino acid or an acid halide under suitable acylation conditions to form a compound of structural formula (I). Ring cyclization to form the diketopiperazine is accomplished by intramolecular amine attack on the ester. A compound (I) also can be derived from a compound (V) having a side chain bearing a leaving group that can react with a primary amine.

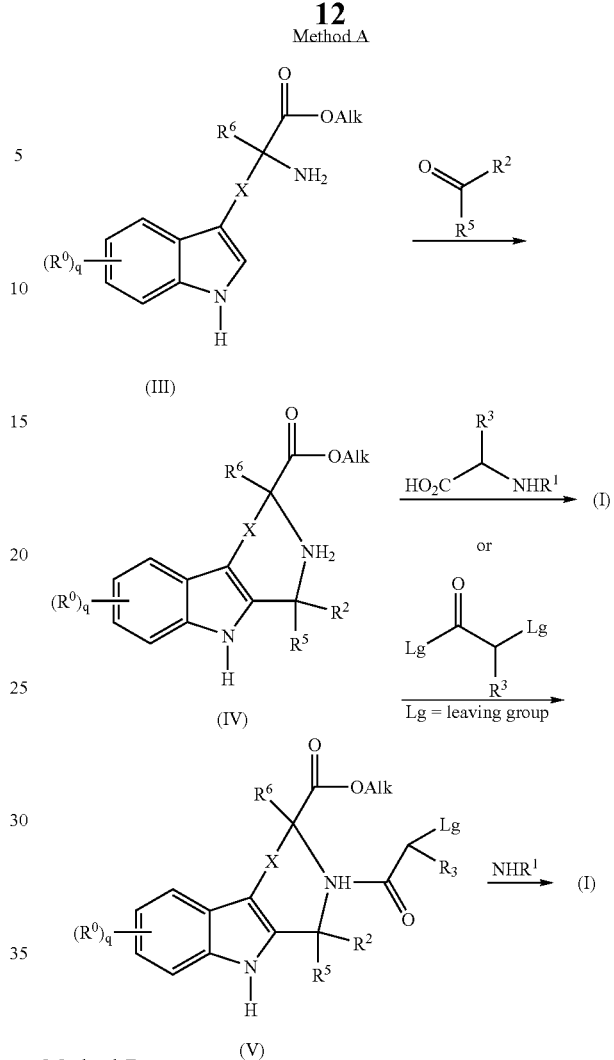

Method B

Alternatively, a compound of structural formula (I) can be prepared first by reaction of a tryptophan (VI) with an amino acid under typical peptide coupling conditions to form an N-acyltryptophan (VII). Ring cyclization to form a diketopiperazine (VIII) is accomplished by intramolecular amine attack on the ester. The resulting piperazine can undergo a condensation with an aldehyde or ketone under modified Pictet-Spengler conditions to give a compound of formula (I). See T. A. Miller et al., *Bioorg. Med. Chem. Lett.*, 8, p. 1065 (1998); A. Previero et al., *Canadian J. of Chemistry*, 46, p. 3404 (1968); and D. Ducrot et al., *Tet Lett.*, 40, p. 9037 (1999).

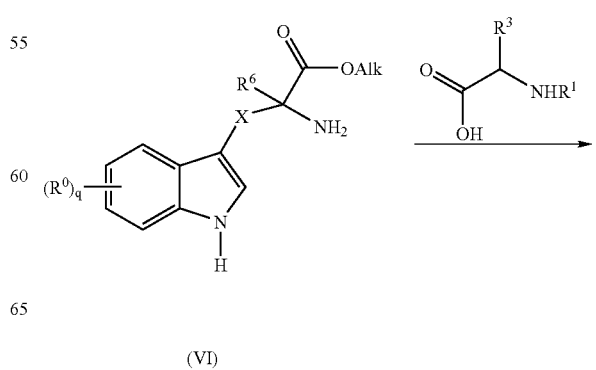

-continued

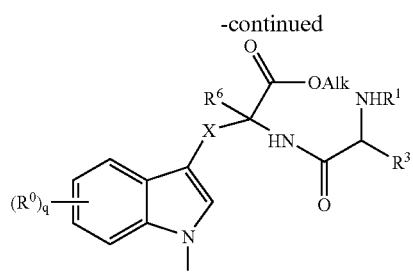

(VII)

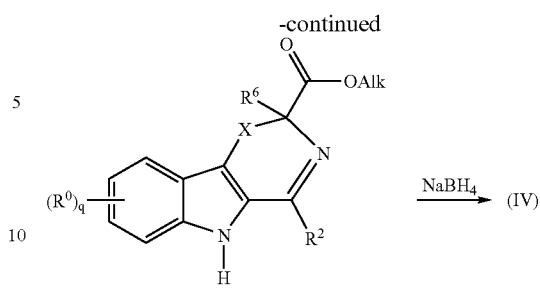

(XI)

Modified Method C

A modified method C avoids racemisation wherein the amine (IX) is first acylated to provide (X), and then converted to the thioamide (XII) with, for example, Lawesson's reagent. Treatment of thioamide (XII) with an alkyl halide or acyl halide leads to an iminium halide (XIII). Reduction of the crude (XIII) with NaBH$_4$ at a reduced temperature leads stereoselectively to the 1,2,3,4,-tetrahydro-β-carboline (IV). Compound (IV) then is converted to a compound (I) using Method A.

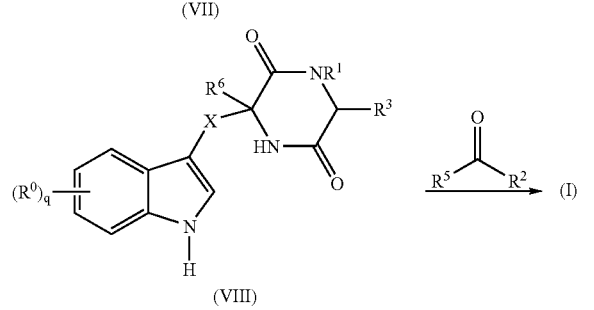

(VIII)

Method C

The β-carboline skeleton can also be constructed using the Bischler-Napieralski reaction which includes a cyclodehydration of an acylated tryptophan (X). See W. M. Whaley et al., "The Preparation of 3,4-Dihydroisoquniolines and Related Compounds by the Bischler-Napieralski Reaction," *Org. React.*, VI, pp. 74–150 (1951); A. Ishida et al., *Chem. Pharm. Bull*, 30, p. 4226 (1982); T. Nakamura et al., *Chem. Pharm. Bull*, 32, p. 2859 (1984); and A. Ishida et al., *Chem. Pharm. Bull*, 33, p. 3237 (1985). P$_2$O$_5$ or POCl$_3$ are the most commonly used cyclization reagents. Reduction of the imine (XI) with sodium borohydride (NaBH$_4$), for example, gives the 1,2,3,4-tetrahydro-β-carboline (IV). Compound (IV) then is converted to a compound of structural formula (I) using Method A, for example.

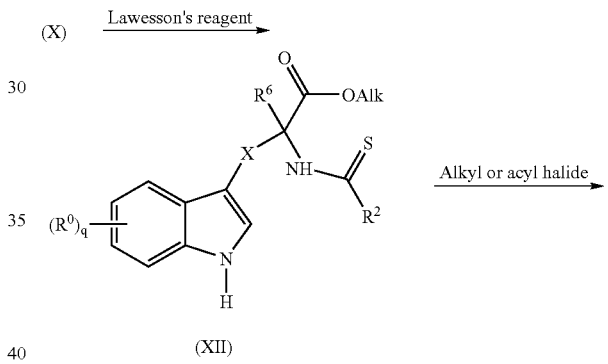

(XII)

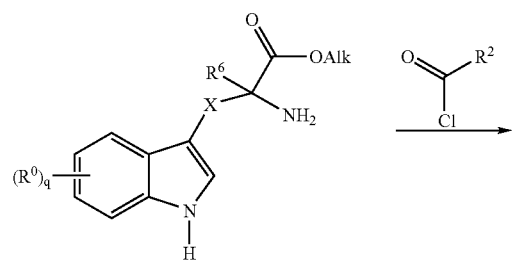

(IX)

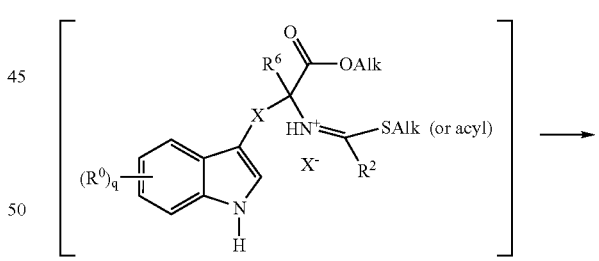

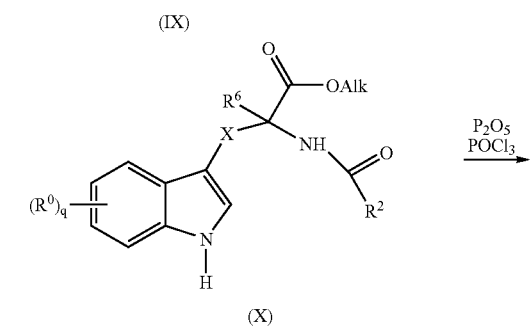

(X)

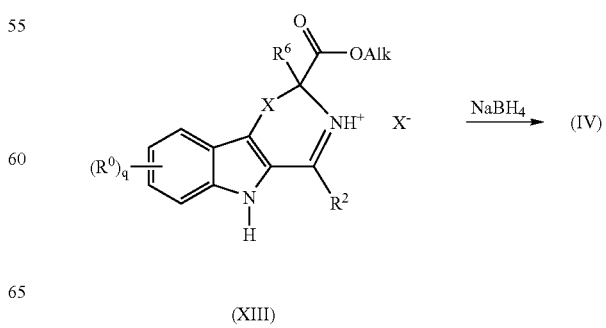

(XIII)

Method D

Synthesis of a C-12,13 dehydro derivative (XIV) has been reported by oxidation with DDQ in aqueous acetonitrile. See M. Nakagawa et al., *Chem. Pharm. Bull*, 37, p. 23 (1989). The 13-hydroxy compound (XV) was obtained as a side product. Further oxidation to the 12,13-diol (XVI) was accomplished with NBS.

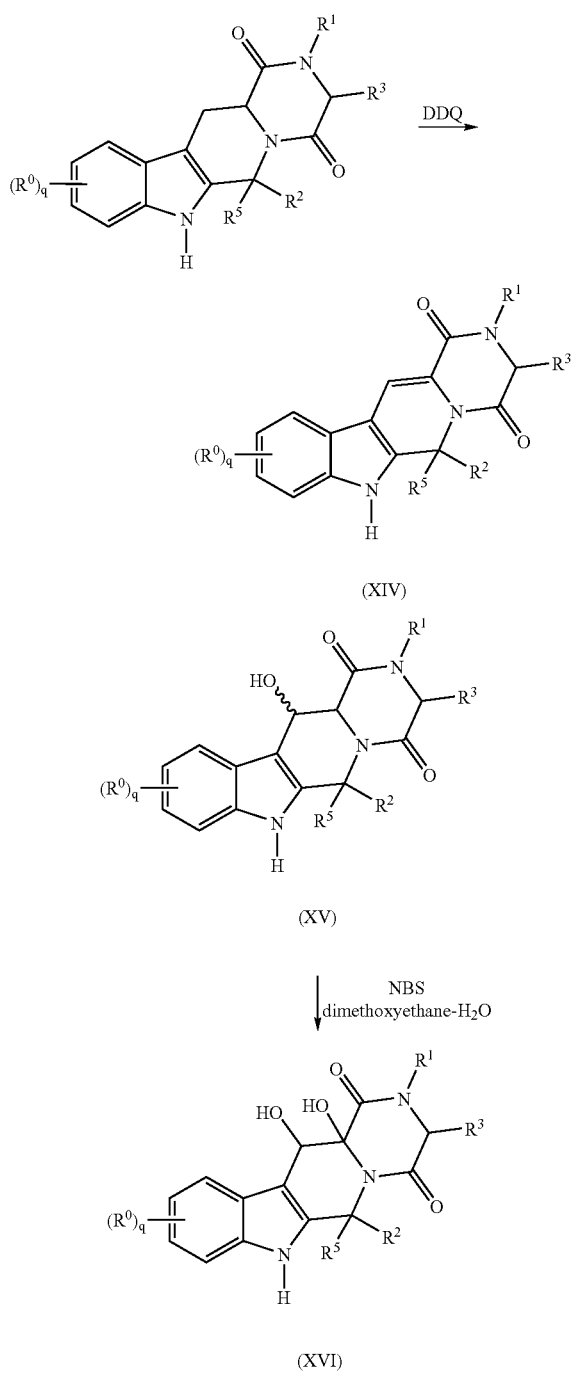

(XIV)

(XV)

(XVI)

It should be understood that protecting groups can be utilized in accordance with general principles of synthetic organic chemistry to provide compounds of structural formula (I). Protecting group-forming reagents, like benzyl chloroformate and trichloroethyl chloroformate, are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) not specifically exemplified herein can be prepared by persons skilled in the art.

In addition, compounds of formula (I) can be converted to other compounds of formula (I). Thus, for example, a particular R substituent can be interconverted to prepare another suitably substituted compound of formula (I). Examples of appropriate interconversions include, but are not limited to, $OR^a$ to hydroxy by suitable means (e.g., using an agent such as $SnCl_2$ or a palladium catalyst, like palladium-on-carbon), or amino to substituted amino, such as acylamino or sulphonylamino, using standard acylating or sulfonylating conditions.

Compounds of formula (I) can be prepared by the method above as individual stereoisomers or as a racemic mixture. Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following additional abbreviations are used hereafter in the accompanying examples: rt (room temperature), aq (aqueous), min (minute), h (hour), g (gram), mmol (millimole), m.p. (melting point), LiOH (lithium hydroxide), eq (equivalents), L (liter), mL (milliliter), μL (microliter), DMSO (dimethyl sulfoxide), $CH_2Cl_2$ (dichloromethane), IPA (isopropyl alcohol), TFA (trifluoroacetic acid), EtOH (ethanol), MeOH (methanol), DMF (dimethylformamide), $NaBH_4$ (sodium borohydride), $MgBr_2$ (magnesium bromide), $Et_3N$ (triethylamine), $MeNH_2$ (methylamine), AcOH (acetic acid), HCl (hydrochloric acid), $Na_2SO_4$ (sodium sulfate), EtOAc (ethyl acetate), $NaHCO_3$ (sodium bicarbonate), $Et_2O$ (diethyl ether), NaOH (sodium hydroxide), $CHCl_3$ (chloroform), $Et_3N$ (triethylamine), $CH_3CN$ (acetonitrile), and THF (tetrahydrofuran).

EXAMPLE 1

(6R,12aR)-6-Benzo[1,3]dioxol-5-yl-2,12a-dimethyl-2,3,6,7,12,12a-hexahydro-pyrazino-[1,2':1,6]pyrido[3,4-b]indole-1,4-dione

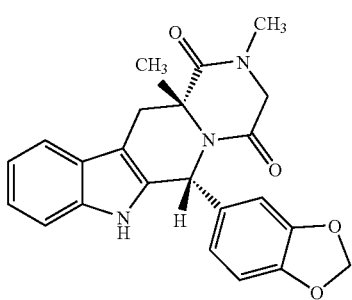

Example 1 was prepared from D-alpha-methyl tryptophan ethyl ester as illustrated in the following synthetic scheme. Intermediate 1 can be prepared by the procedure disclosed in Daugan U.S. Pat. No. 5,859,006.

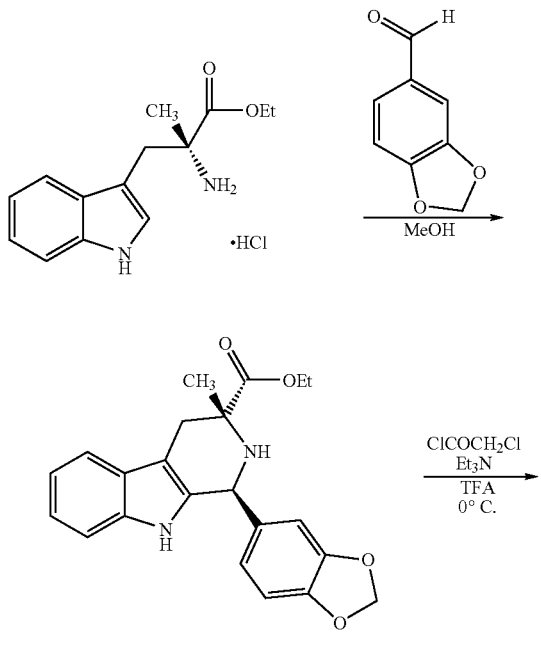

Intermediate 1

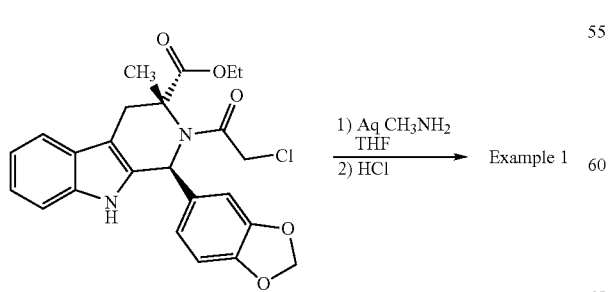

Intermediate 2

Preparation of (+/−)-cis-2-chloroacetyl-β-carboline (Intermediate 2)

Chloroacetyl chloride (0.16 mL, 2.14 mmol) was added dropwise to a mixture of Intermediate 1 (0.31 g, 0.82 mmol) and $Et_3N$ (0.46 mL, 3.28 mmol) in THF (5 mL) at 0° C. under a nitrogen blanket. The resulting mixture was warmed to room temperature and stirred for about 4 h. The reaction was quenched with 1 N HCl (2 mL), then concentrated to remove THF. The residue was diluted with $CH_2Cl_2$ (50 mL) and water (3 mL). The layers were separated, and the organic was washed with water (5 mL) and brine (5 mL), then dried over anhydrous $Na_2SO_4$. Filtration and concentration in vacuo gave a brown oil. Purification by column chromatography (silica gel, 0–10% $EtOAc/CH_2Cl_2$) afforded Intermediate 2 as a light brown solid 0.25 g (66.2%); TLC $R_f$ (10% $EtOAc/CH_2Cl_2$)=0.52.

$^1$H NMR (300 MHz, $CDCl_3$) δ: 11.31 (s, 1H), 7.46–7.48 (m, 2H), 7.33–7.39 (m, 2H), 7.07 (dt, J=1 Hz, J=7.5 Hz, 1H), 6.91–7.00 (m, 2H), 6.18 (s, 1H), 5.98 (dd, J=0.8 Hz, J=6.8 Hz, 2H), 4.62 (d, J=14.1 Hz, 1H), 4.13–4.27 (m, 2H), 3.84 (d, J=14.1 Hz, 1H), 3.10 (s, 2H), 1.34 (s, 3H), 1.29 (t, J=7.1 Hz, 3H)

PREPARATION OF EXAMPLE 1

A mixture of Intermediate 2 (0.248 g, 0.54 mmol), 40% $CH_3NH_2$ in water (0.24 mL, 2.73 mmol), and THF (2 mL) was heated at 40° C. under a nitrogen blanket for 4h, during which time a white precipitate was formed. The suspension was cooled to room temperature, then quenched with concentrated HCl (0.13 mL). The THF was removed in vacuo and 10% water/MeOH (1 mL) was added to the residue. The solid was collected by filtration to afford 0.15 g (68.0%) of Example 1 after drying: mp 327–332° C.; TLC $R_f$ (10% $EtOAc/CH_2Cl_2$)=0.23.

$^1$H NMR (300 MHz, DMSO-$d_6$) δ: 10.96 (s, 1H), 7.52 (d, J=7.5 Hz, 1H), 7.29 (d, J=7.8 Hz, 1H), 7.05 (dt, J=1.1 Hz, J=7.5 Hz, 1H), 6.98 (dt, J=1.1 Hz, J=7.4 Hz, 1H), 6.86 (s, 1H), 6.75–6.82 (m, 2H), 6.02 (s, 1H), 5.92 (d, J=1.0 Hz, 2H), 4.31 (d, J=18.2 Hz, 1H), 4.01 (d, J=18.1 Hz, 1H), 3.37 (d, J=15.9 Hz, 1H), 3.17 (d, J=1.59 Hz, 1H), 2.95 (s, 3H), 1.29 (s, 3H); MS (API) m/z 404 (M+H), 426 (M+Na); $[\alpha]_D^{25°}$ c.=+62.2° (c=0.21, DMSO). Anal. Calcd. for $C_{23}H_{31}N_3O_4$; C, 68.47; H, 5.25; N, 10.42. Found: C, 68.20; H, 5.33; N, 10.35. The relative stereochemistry of the major product was confirmed to be the cis isomer by NOE difference experiments (DMSO-$d_6$): positive NOE enhancements from the C12a methyl at 1.29 ppm to the C6 proton at 6.02 ppm.

EXAMPLES 2a AND 2b

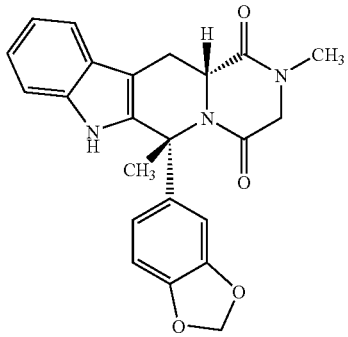

EXAMPLE 2a (+−, Cis)-6-Benzo[1,3]dioxol-5-yl-2,6-dimethyl-2,3,
6,7,12,12a-hexahydropyrazino-[1',2':1,6]pyrido[3,4-
b]indole-1,4-dione

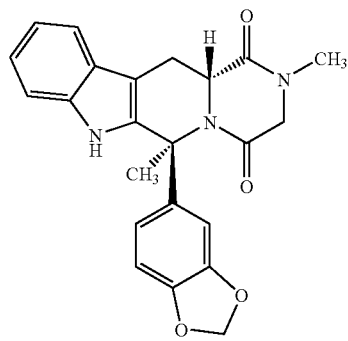

EXAMPLE 2b (+−, trans)-6-Benzo[1,3]dioxol-5-yl-2,6-dimethyl-2,
3,6,7,12,12a-hexahydropyrazino-[1',2':1,6]pyrido[3,
4-b]indole-1,4-dione Examples 2a and 2b were prepared from D-tryptophan methyl ester and 3',4'-(methylenedioxy)acetophenone as depicted in the following scheme.

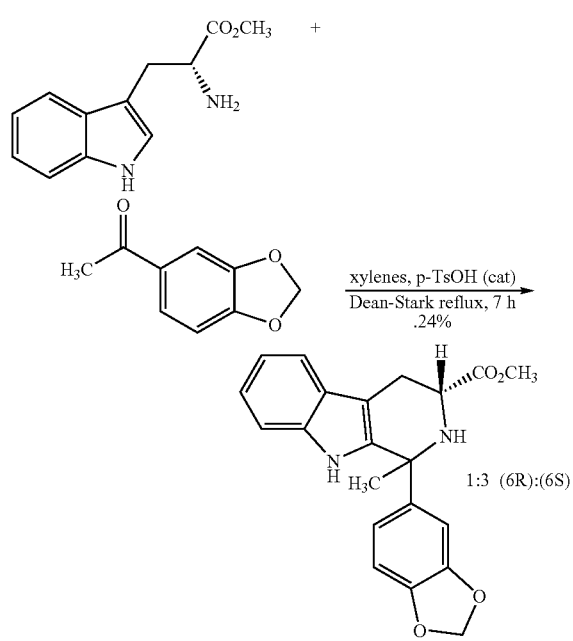

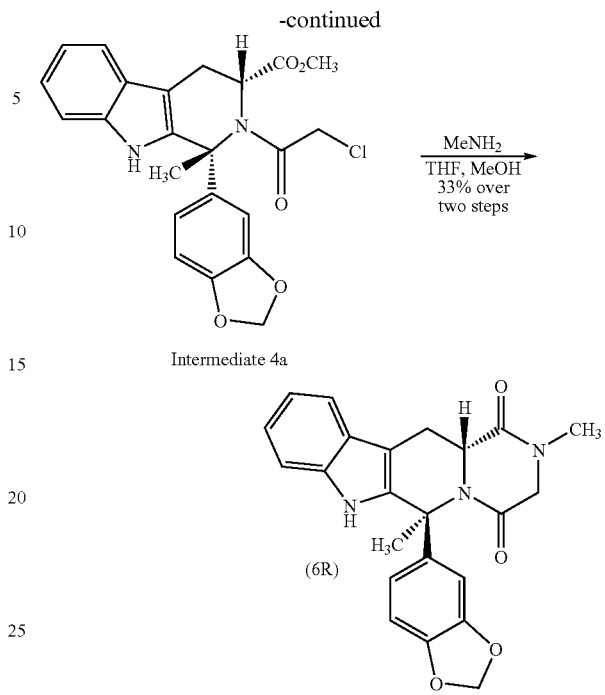

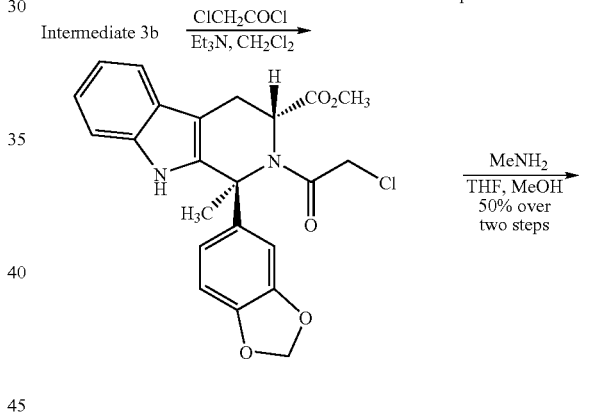

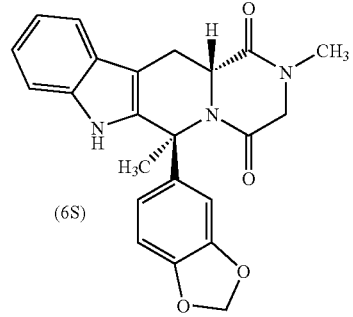

Preparation of (6R)-Carboline (Intermediate 3a) and (6S)-Carboline (Intermediate 3b)

A mixture of D-tryptophan methyl ester (3.25 g, 15.2 mmol) and 3',4'-(methylenedioxy)acetophenone in xylenes was heated at reflux under a nitrogen blanket with a Dean-Stark condenser for 20 hours. The yellow mixture was cooled to room temperature, and p-toluenesulfonic acid monohydrate (0.25 g) was added. The mixture then was reheated to reflux for an addition 7 hours. The dark brown mixture was cooled to room temperature and diluted with EtOAc (100 mL). The mixture then was washed successively with saturated NaHCO$_3$ (15 mL), water (20 mL), and brine (20 mL), dried over Na$_2$SO$_4$, filtered, and the solvent was removed under reduced pressure. The resulting brown oil was purified by flash column chromatography, eluting with CH$_2$Cl$_2$/EtOAc (9:1), to provide isomer Intermediate 3a as a yellow solid (397 mg, 6%): TLC R$_f$ (9:1 CH$_2$Cl$_2$/MeOH)=0.61.

$^1$H NMR (300 MHz, CDCl$_3$) δ: 7.56–7.49 (m, 2H), 7.25–7.09 (m, 3H), 6.95–6.88 (m, 2H), 6.75 (d, J=8.3 Hz, 1H), 5.91 (s, 2H), 4.08–3.98 (m, 1H), 3.77 (s, 3H), 3.24–3.16 (m, 1H), 2.95–2.82 (m, 1H), 1.87 (s, 3H). The later eluting isomer Intermediate 3b then was obtained as a yellow solid (1.17 g, 18%): TLC R$_f$ (9:1 CH$_2$Cl$_2$/MeOH)=0.51. $^1$H NMR (300 MHz, CDCl$_3$) δ: 7.92 (bs, 1H), 7.56 (d, J=8.3 Hz, 1H), 7.38 (d, J=8.3 Hz, 1H), 7.26–7.10 (m, 2H), 6.87 (s, 1H), 6.66 (d, J=8.0 Hz, 1H), 6.58 (d, J=8.0, 1H), 5.92 (s, 2H), 3.77 (s, 3H), 3.67–3.58 (m, 1H), 3.17–3.07 (m, 1H), 2.91–2.79 (m, 1H), 1.81 (s, 3H)

Preparation of (6R)-2-Chloroacetyl-β-carboline (Intermediate 4a)

Chloroacetyl chloride (0.12 mL, 1.5 mmol) was added dropwise to a mixture of the (6R)-carboline Intermediate 3a (364 mg, 1.00 mmol) and Et$_3$N (0.21 mL, 1.5 mmol) in CH$_2$Cl$_2$ (10 mL) at 0° C. under a nitrogen blanket. The resulting mixture was stirred at 0° C. for 1 hour, after which the mixture was stirred at room temperature for another 1 hour. The brown solution was diluted with CH$_2$Cl$_2$ (30 mL), then washed successively with saturated NaHCO$_3$ (10 mL) and brine (10 mL). The organic layer was dried over Na$_2$SO$_4$, filtered, and the solvent was removed under reduced pressure to provide a thick brown oil. The residue was purified by flash column chromatography, eluting with CH$_2$Cl$_2$/EtOAc (10:1), to provide (6R)-2-chloroacetyl-β-carboline (Intermediate 4a) as a brown oil, which was used in the next step (297 mg): TLC R$_f$ (CH$_2$Cl$_2$)=0.42.

PREPARATION OF EXAMPLE 2a

A mixture of Intermediate 4a (295 mg, 0.67 mmol), CH$_3$NH$_2$ (1.4 mL, 2.0 M in THF, 2.8 mmol) and MeOH (7 mL) was heated at 45° C. under a nitrogen blanket for 18 hours. The resulting yellow slurry was cooled to room temperature and the precipitate was collected by vacuum filtration. The solid was washed with CH$_3$OH (2×2 mL), then the solid was dried in a vacuum oven at 80° C. for 6 hours to provide Example 2a as a white powder (135 mg, 33% for two steps). The powder was confirmed to be the desired cis-isomer by NOE difference experiment (positive enhancement): mp 319–3230° C.; TLC R$_f$ (9:1 CH$_2$Cl$_2$/EtOAc)=0.15.

$^1$H NMR (300 MHz, CDCl$_3$) δ: 7.58–7.50 (m, 1H), 7.41 (bs, 1H), 7.22–7.07 (m, 3H), 6.93–6.87 (m, 1H), 6.76–6.66 (m, 2H), 5.89 (s, 1H), 5.85 (2, 1H), 4.50–4.40 (m, 1H), 3.99 (d, J=17.4 Hz, 1H), 3.89–3.73 (m, 2H), 3.17–3.08 (m, 1H), 3.02 (s, 3H), 2.15 (s, 3H); $^{13}$C NMR (75 MHz, CDCl$_3$) δ: 165.2, 162.5, 147.9, 146.3, 138.8, 137.5, 136.6, 122.5, 120.0, 118.7, 117.9, 111.0, 107.8, 106.0, 101.1, 62.7, 55.8, 52.2, 33.3, 27.3, 21.4 ppm; API MS m/z 404 [C$_{23}$H$_{21}$N$_3$O$_4$+H]$^+$; [α]$_D^{25°\,C.}$=+3.3 (c=0.5, CHCl$_3$). Anal. Calcd. for C$_{23}$H$_{21}$N$_3$O$_4$: C, 68.47; H, 5.25; N, 10.42. Found: C, 68.41; H, 5.25; N, 10.13.

Preparation of (6S)-2-Chloroacetyl-β-carboline (Intermediate 4b)

Chloroacetyl chloride (0.29 mL, 3.6 mmol) was added dropwise to a mixture of the (6S)-carboline Intermediate 3b (1.09 g, 2.99 mmol) and Et$_3$N (0.51 mL, 3.59 mmol) in CH$_2$Cl$_2$ (30 mL) at 0° C. under a nitrogen blanket. The resulting mixture was stirred at 0° C. for 0.5 hour, after which the mixture was stirred at room temperature for another 2.5 hours. The brown-reddish solution was diluted with CH$_2$Cl$_2$ (30 mL) and washed successively with saturated NaHCO$_3$ (15 mL) and brine (30 mL). The organic layer was dried over Na$_2$SO$_4$, filtered, and the solvent was removed under reduced pressure to provide a brown solid. The residue was purified by flash column chromatography, eluting with CH$_2$Cl$_2$ to provide (6S)-2-chloroacetyl-β-carboline Intermediate 4b as a brown solid, which was used in the next step without further purification (780) mg): TLC R$_f$ (CH$_2$Cl$_2$)=0.29.

PREPARATION OF EXAMPLE 2b

A mixture of Intermediate 4b (770 mg, 1.75 mmol), CH$_3$NH$_2$ (3.5 mL, 2.0 M in THF, 7.0 mmol) and CH$_3$OH (10 mL) was heated at 40° C. under a nitrogen blanket for 30 hours. The resulting yellow solution was cooled to room temperature, then concentrated under reduced pressure. The residue was purified by flash column chromatography, eluting with CH$_2$Cl$_2$/EtOAc (10:1), to afford Example 2b as a white powder (601 mg, 50% for two steps): mp 212–219° C.; TLC R$_f$ (9:1 CH$_2$Cl$_2$/EtOAc)=0.31.

$^1$H NMR (300 MHz, CDCl$_3$) δ: 7.81 (bs, 1H), 7.56 (d, J=6.9 Hz, 1H), 7.30–7.06 (m, 3H), 6.88 (d, J=1.7 Hz, 1H), 6.80 (d, J=8.1 Hz, 1H), 6.69 (d, J=8.1 Hz, 1H), 5.92 (d, J=1.2 Hz, 1H), 5.90 (d, J=1.0 Hz, 1H), 4.37–4.24 (m, 1H), 4.01 (d, J=17.8 Hz, 1H), 3.81 (d, J=1.2 Hz, 1H), 5.90 (d, J=1.0 Hz, 1H), 4.37–4.24 (m, 1H), 4.01 (d, J=8.1 Hz, 1H), 3.77–3.62 (m, 1H), 3.05–2.87 (m, 4H), 2.33 (s, 3H); $^{13}$C NMR (75 MHz, CDCl$_3$) δ: 165.5, 163.0, 148.0, 147.3, 137.2, 136.6, 136.2, 126.1, 122.6, 120.4, 120.0, 118.6, 111.1, 107.8, 107.5, 101.3, 64.3, 56.7, 52.6, 33.2, 28.0, 26.8 ppm; API MS m/z 404 [C$_{23}$H$_{21}$N$_3$O$_4$+H]$^+$; [α]$_D^{25°\,C.}$=+1.43 (c=0.5, CHCl$_3$). Anal. Calcd. for C$_{23}$H$_{21}$N$_3$O$_4$·0.75H$_2$O: C, 66.26; H, 5.44; N, 10.08. Found: C, 66.53; H, 5.30; N, 9.97.

EXAMPLE 3

(+−, 6,12a cis-12,12a-trans)-6-Benzo-(1,3)-dioxol-5-yl-methyl-12-phenyl-2,3,6,7,12,12a-hexahydro-pyrazino[1',2':1,6]pyrido[3,4-b]indole-1,4-dione

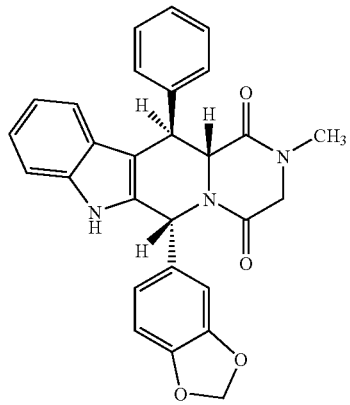

Example 3 was prepared as depicted in following Schemes 1 through 3. See T. Nagy, *Eur. J. Med. Chem.*, 30, p. 575 (1995). Erythro isomer (+/−) Intermediate 5a and threo isomer (+/−) Intermediate 5b were prepared from indole. The separated isomers were separately used to provide Example 3, as shown in Scheme 2 and Scheme 3, respectively. In the case of erythro isomer Intermediate 5a, epimerization in the final step was observed to provide the inverted stereochemistry at C12.

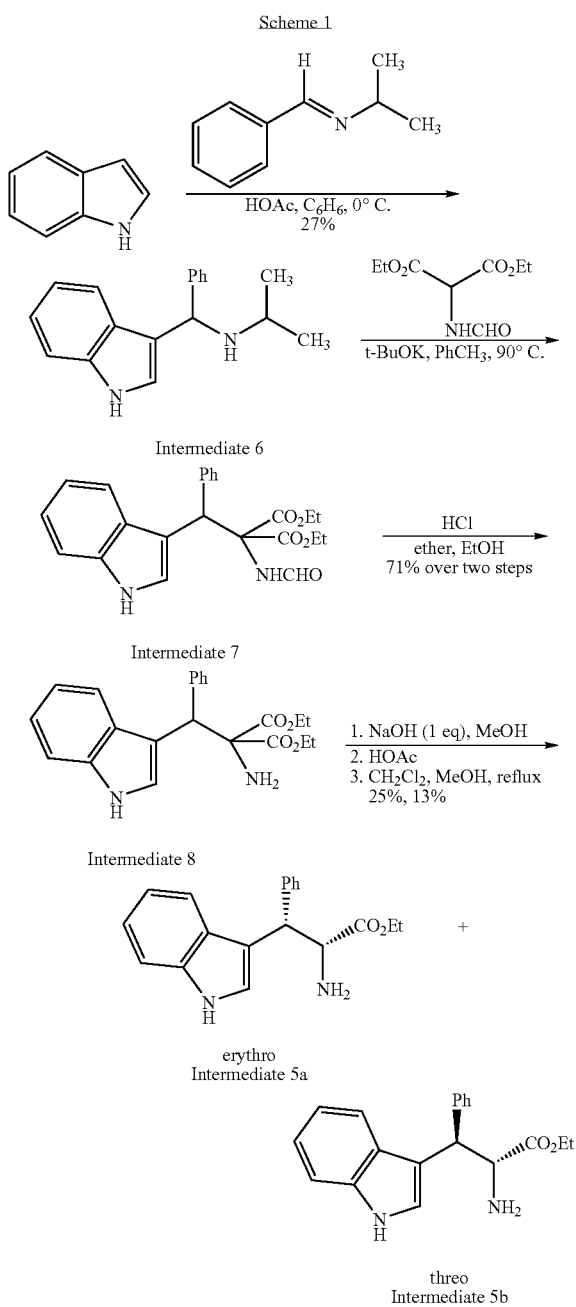

Preparation of Gramine (Intermediate 6)

To a solution of N-benzylideneisopropylamine (7.5 g, 51 mmol) in benzene (10 mL) at 0° C. under a nitrogen blanket was added a solution of indole (5.0 g, 43 mmol) AcOH (30 mL) over a 3-hour period, after which the stirring was continued at 0° C. for an additional 3 hours. The bulk of the solvent was removed under reduced pressure and the remaining reaction mixture was poured into 400 mL of ice water. The mixture was extracted with $Et_2O$ (3×75 mL), and the aqueous layer was cooled to 0° C. and made basic with 30% aqueous NaOH to a pH 11–12 range. The precipitate was extracted with $CH_2Cl_2$ (2×75 mL) and the combined organic extracts were dried over $Na_2SO_4$, filtered, and the solvent was removed under reduced pressure to provide gramine Intermediate 6 as a yellow semisolid (3.06 g, 27%): TLC $R_f$ (1:1 $CH_2Cl_2$/EtOAC)=0.45.

$^1$H NMR (300 MHz, $CDCl_3$) δ: 7.97 (br s, 1H), 7.62 (d, J=8.0 Hz, 1H), 7.47 (d, J=6.0 Hz, 1H), 7.36–7.02 (m, 6H), 6.96 (d, J=2.8 Hz, 1H), 5.27 (s, 1H), 2.85 (sep, J=7.0 Hz, 1H), 1.17 (d, J=7.0 Hz, 3H), 1.08 (d, J=7.0 Hz, 3H).

Preparation of N-Formylaminomalonate (Intermediate 7)

A mixture of Intermediate 6 (5.8 g, 22 mmol), diethyl N-formylaminomalonate (4.64 g, 23 mmol), and potassium tert-butoxide (256 mg. 2.3 mmol) in toluene (85 mL) was heated at 90–100° C. for 48 hours. A slow stream of nitrogen was bubbled through the reaction mixture to eliminate the cleaved isopropylamine. The reaction mixture was cooled to room temperature and diluted with a mixture of toluene (50 mL) and EtOAc (60 mL). The organic mixture was washed successively with water (20 mL), 1 N HCl (15 mL), water (20 mL), and brine (15 mL). The organic layer was dried over $Na_2SO_4$, filtered, and the solvent was removed under reduced pressure to afford N-formylaminomalonate Intermediate 7 as a brown foam-like solid which was suitable to use without further purification (9.1 g, 100%): TLC $R_f$ (1:1 $CH_2Cl_2$/EtOAc)=0.75.

$^1$H NMR (300 MHz, $CDCl_3$) δ: 8.46 (br s, 1H), 8.06 (s, 1H), 7.65–6.87 (m, 11H), 5.76 (s, 1H), 5.62 (s, 1H), 4.23–3.81 (m, 4H), 1.45–0.88 (m, 6H).

Preparation of Aminomalonate (Intermediate 8)

To a solution of Intermediate 7 (9.1 g, 22 mmol) in $CH_3OH$ (200 mL), was added a solution of HCl (45 mL, 45 mmol, 1 N solution in $Et_2O$), after which the reaction mixture was kept at room temperature without stirring for 21 hours. The solvent was removed under reduced pressure, then the residue was diluted with $CH_2Cl_2$ (200 mL). The mixture was washed with $NaHCO_3$ solution (2×20 mL), water (20 mL), and brine (20 mL). The organic layer was dried over $Na_2SO_4$, filtered, and the solvent was removed under reduced pressure to provide a red oil which was purified by flash column chromatography, eluting with $CH_2Cl_2$/EtOAc, to provide aminomalonate Intermediate 8 as an amber solid (6.0 g, 71%): TLC $R_f$ (20:1 $CH_2Cl_2$/EtOAc) =0.71.

$^1$H NMR (300 MHz, $CDCl_3$) δ: 8.03 (br s, 1H), 7.78 (d, J=2.7 Hz, 1H), 7.56–6.95 (m, 9H), 5.46 (s, 1H), 4.15 (q, J=7.5 Hz, 2H), 3.95 (q, J=7.5 Hz, 2H), 2.20 (br s, 2H), 1.21 (t, J=7.5 Hz, 3H), 0.85 (t, J=7.5 Hz, 3H).

Preparation of (+/−)-β-Phenyltryptophan Intermediates 5a and 5b

To a solution of Intermediate 8 (5.31 g, 14 mmol) in $CH_3OH$ (56 mL) and water (16 mL) was added a solution of NaOH (0.61 g, 15 mmol) in water (2 mL), and the mixture was stirred at room temperature for 5 days. The resulting mixture was concentrated under reduced pressure (bath temperature 25° C.) to a volume of 30 mL and the resulting residue was diluted with water (250 mL). The milky mixture was extracted with $Et_2O$ (3×50 mL) to remove unreacted starting malonate, and the aqueous layer was cooled to in an ice bath and acidified with AcOH to pH 4. The precipitate was filtered under reduced pressure to provide 3.2 g of a solid that was dried in air for several hours. The aqueous filtrate was concentrated to 20 mL, then extracted with $CH_2Cl_2$ (70 mL). The organic layer was washed with brine, dried over $Na_2SO_4$, filtered, and concentrated over reduced pressure to afford a 1:1 mixture of Intermediates 5a and 5b.

The precipitated solid was dissolved in a mixture of $CH_2Cl_2$/MeOH (2:1, 40 mL) and was heated to reflux for 1.5 hours to promote decarboxylation. The resulting solution was concentrated to provide a yellow solid, which was combined with the mixture of Intermediates 5a and 5b. The resulting solid mixture was dissolved in a mixture of (10:1, 20 mL), and allowed to stand at room temperature for 1 hour. The white precipitate was filtered under reduced pressure to afford a second crop of Intermediate 5a as a white solid (0.46 g). The filtrate was concentrated and the residue was purified by flash column chromatography, eluting with $CH_2Cl_2$/MeOH (20:1), to provide threo isomer (+/−) Intermediate 5b as a white solid (587 mg, 13%): TLC $R_f$ (20:1 $CH_2Cl_2$/MeOH)=0.50.

$^1$H NMR (300 MHz, $CDCl_3$) δ: 8.18 (br s, 1H), 7.40–6.97 (m, 10H), 4.68 (d, J=6.7 Hz, 1H), 4.27 (d, J=6.7 Hz, 1H), 4.05 (q, J=7.6 Hz, 2H), 2.08 (s, 2H), 1.07 (t, J=7.6 Hz, 3H).

The overall yield of the isolated erythro isomer Intermediate 5a was 25%: TLC $R_f$ (20:1)=0.43.

$^1$H NMR (300 MHz, $CDCl_3$) δ: 8.18 (br s, 1H), 7.47–6.97 (m, 10H), 4.66 (d, J=8.5 Hz, 1H), 4.23 (d, J=8.5 Hz, 1H), 3.95 (q, J=7.6 Hz, 2H), 2.06 (s, 2H), 0.96 (t, J=7.6 Hz, 3H).

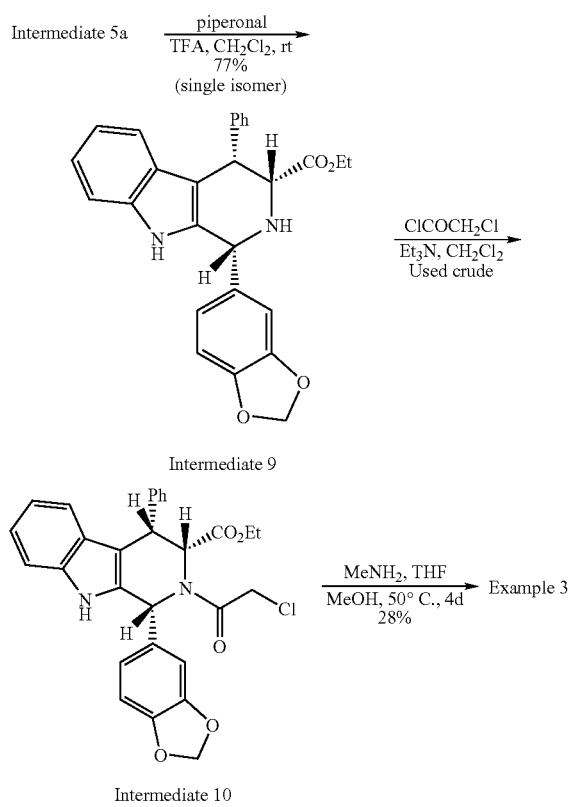

Scheme 2

Intermediate 10

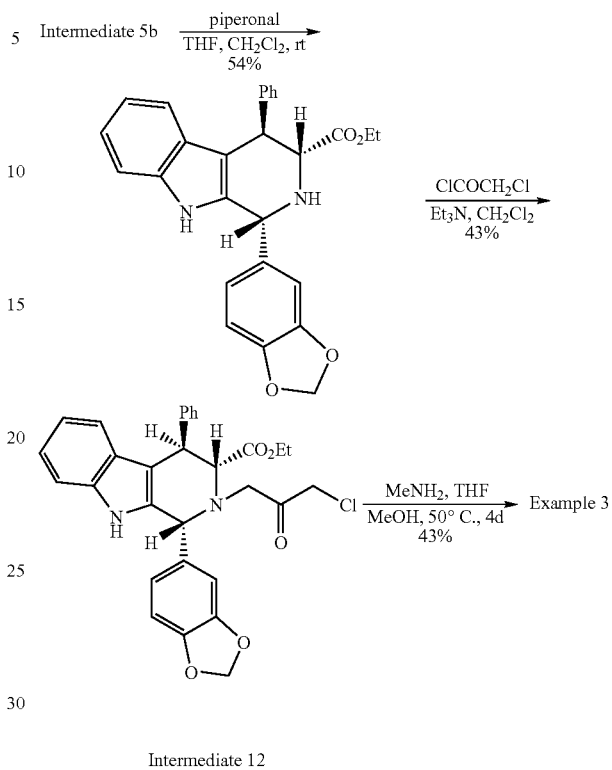

Scheme 3

Intermediate 12

Preparation of cis-β-Carboline Intermediate 9

Trifluoroacetic acid (0.263 mL, 3.40 mmol) was added to a mixture of Intermediate 5a (500 mg. 1.62 mmol) and piperonal (292 mg, 1.94 mmol) in $CH_2Cl_2$ (10 mL) at 0° C. under a nitrogen blanket, after which the mixture was warmed to room temperature and stirred for 6 hours. The reaction mixture was diluted with $CH_2Cl_2$ (80 mL) and neutralized with saturated $NaHCO_3$ solution (10 mL). The organic layer was washed with brine (10 mL), dried over $Na_2SO_4$, filtered, and the solvent was removed under reduced pressure to provide a yellow solid. The residue was purified by flash column chromatography, eluting with $CH_2Cl_2$/EtOAc (10:1), to provide (+/−)-cis-β-carboline Intermediate 9 as a yellow solid (535 mg. 77%): TLC $R_f$ (10:1 $CH_2Cl_2$/EtOAc)=0.40.

$^1$H NMR (300 MHz, $CDCl_3$) δ: 7.55 (br s, 1H), 7.32–7.12 (m, 7H), 7.06 (t, J=8.3 Hz, 1H), 6.90 (d, J=8.3 Hz, 1H), 6.85–6.75 (m, 3H), 6.58 (d, J=8.5 Hz, 1H), 5.97 (s, 2H), 5.32 (s, 1H), 4.51–4.43 (m, 1H), 4.08–3.94 (m, 2H), 3.89–3.79 (m, 1H), 1.02 (t, J=7.7 Hz, 3H).

Preparation of cis-2-Chloroacetyl-β-carboline Intermediate 10

Chloroacetyl chloride (0.120 mL, 1.51 mmol) was added dropwise to a mixture of Intermediate 9 (510 mg. 1.16 mmol) and $Et_3N$ (0.211 mL, 1.51 mmol) in $CH_2Cl_2$ (6 mL) at 0° C. under a nitrogen blanket, and the resulting mixture was stirred at 0° C. for 2 hours. The yellow solution was diluted with $CH_2Cl_2$ (80 mL), washed with saturated $NaHCO_3$ solution (10 mL) and brine (10 mL), and the solvent was removed under reduced pressure to provide Intermediate 10 as a yellow solid which was suitable for use without further purification (600 mg): TLC $R_f$ (10:1 $CH_2Cl_2$/EtOAc)=0.94.

Preparation of cis-β-Carboline Intermediate 11

Trifluoroacetic acid (0.304 mL, 3.95 mmol) was added to a mixture of Intermediate 5b (580 mg. 1.88 mmol) and piperonal (338 mg, 2.26 mmol) in CH$_2$Cl$_2$ (10 mL) at 0° C. under a nitrogen blanket, after which the mixture was warmed up to room temperature and stirred for 3 days. The reaction mixture was diluted with CH$_2$Cl$_2$ (60 mL) and neutralized with saturated NaHCO$_3$ solution (5 mL). The organic layer was dried over Na$_2$SO$_4$, filtered, and the solvent was removed under reduced pressure. The residue was purified by flash column chromatography, eluting the hexanes/EtOAc (2:1) to provide Intermediate 11 as a clear viscous oil which was used without characterization (435 mg, 54%): TLC R$_f$ (2:1 hexanes/EtOAc)=0.51.

Preparation of cis-2-Chloroacetyl-β-carboline Intermediate 12

Chloroacetyl chloride (0.103 mL, 1.30 mmol) was added dropwise to a mixture of Intermediate 11 (431 mg, 1.00 mmol) and Et$_3$N (0.182 mL, 1.30 mmol) in CH$_2$Cl$_2$ (10 mL) at 0° C. under a nitrogen blanket, and the resulting mixture was stirred at 0° C. for 2 hours, after which it was warmed to room temperature and stirred for an additional 4 hours. The yellow solution was diluted with CH$_2$Cl$_2$ (60 mL), washed with saturated NaHCO$_3$ solution (10 mL), dried over Na$_2$SO$_4$, and filtered. The solvent was removed under reduced pressure to provide a yellow solid, which was dissolved in a small amount of EtOAc, then filtered through a short plug of silica gel to remove triethylamine hydrochloride. The filtrate was concentrated and further purified by a slurry with hexanes/EtOAc/MeOH (2:1:0.2). The while precipitate was collected by filtration under reduced pressure to afford Intermediate 12 as a white solid (235 mg, 43%): TLC R$_f$ (2:1 hexanes/EtOAc)=0.45.

$^1$H NMR (300 MHz, CDCl$_3$) δ: 7.80 (br s, 1H), 7.40–6.76 (m, 10H), 6.56 (s, 1H), 6.04 (s, 1H), 6.02 (s, 1H), 5.20 (s, 1H), 5.02–4.98 (m, 1H), 4.00–3.78 (m, 4H), 3.57–3.43 (m, 1H), 0.98 (t, J=7.6 Hz, 3H); API MS m/z 517 [C$_{29}$H$_{25}$ClN$_2$P$_5$]$^+$.

PREPARATION OF EXAMPLE 3 FROM INTERMEDIATE 10

A mixture of Intermediate 10 (600 mg, 1.16 mmol) and CH$_3$NH$_2$ (2.3 mL, 4.6 mmol, 2 M solution in THF) in MeOH (8 mL) was heated at 50° C. under a nitrogen blanket for 4 days. The resulting brown solution was cooled to room temperature and concentrated under reduced pressure. The residue was purified by flash column chromatography, eluting with hexanes/EtOAc (8:1), followed by a trituration with a small amount of CH$_2$Cl$_2$ to provide Example 3 as a white solid (154 mg, 28%).

PREPARATION OF EXAMPLE 3 FROM INTERMEDIATE 12

A mixture of Intermediate 12 (230 mg, 0.44 mmol) and CH$_3$NH$_2$ (0.84 mL, 1.68 mmol, 2M solution in THF) in MeOH (5 mL) was heated at 45° C. under a nitrogen blanket for 24 hours. The resulting brown product was cooled to room temperature, then the mixture was concentrated under reduced pressure to provide a pink solid, which was triturated with hexanes/EtOAc (1:1) followed by vacuum-filtration. The solid was triturated again with CH$_2$Cl$_2$ followed by vacuum filtration to provide Example 3 as a white solid (130 mg, 63%): mp 295–298° C.; TLC R$_f$ (1:1 hexanes/EtOAc) =0.22.

$^1$H NMR (300 MHz, CDCl$_3$) δ: 7.83 (br s, 1H), 7.55 (d, J=8.0 Hz, 2H), 7.43–7.30 (m, 2H), 7.22 (d, J=8.1 Hz, 1H), 7.05 (t, J=7.5 Hz, 1H), 6.86 (dd, J=8.0, 1.6 Hz, 1H), 6.81–6.69 (m, 3H), 6.39 (s, 1H), 6.16 (d, J=8.3 Hz, 1H), 5.90 (s, 1H), 5.88 (s, 1H), 5.11 (d, J=9.8 Hz, 1H), 4.49 (d, J=9.8 Hz, 1H), 4.17 (d, J=17.0 Hz, 1H), 3.83 (d, J=17.0 Hz, 1H), 2.95 (s, 3H); API MS m/z 466 [C$_{28}$H$_{23}$N$_3$O$_4$+H]$^+$. Anal. Calcd. for C$_{28}$H$_{23}$N$_3$O$_4$: C, 72.24; H, 4.98; N, 9.03. Found C, 71.86; H, 5.10; N, 8.90. The stereochemistry of analog Example 3 was confirmed to be the desired cis isomer by a series of NOE difference experiments: a positive NOE enhancement from the C12a proton at 4.49 ppm to the C6 proton at 6.39 ppm; a positive NOE enhancement from the C6 proton at 6.39 ppm to the C12a proton at 4.49 ppm. Chiral HPLC analysis (Chiralcel OD Column, 250×4.6 mm, Retention Time=13.5 minutes and 17.8 minutes; 1:1 EPA/hexanes; flow=0.5 mL/minute; detector @ 254 nm; 25° C.) showed two major peaks, with a ratio of 1:1 and a total purity of 100%.

EXAMPLES 4a AND 4b

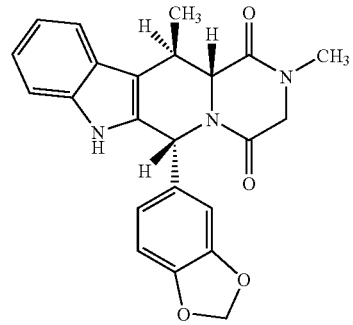

EXAMPLE 4a (+−, cis, trans methyl)-6-Benzo[1,3]dioxol-5-yl-2,12-dimethyl-2,3,6,7,12,12a-hexahydropyrazino[1',2':1,6]pyrido[3,4-b]indole-1,3-dione

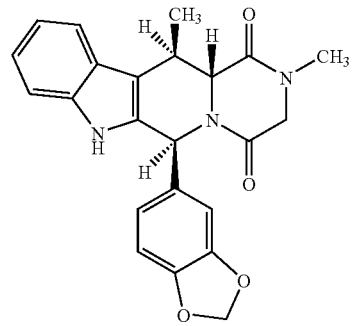

EXAMPLE 4b (+−, trans, trans methyl)-6-Benzo[1,3]dioxol-5-yl-2,12-dimethyl-2,3,6,7,12,12a-hexahydropyrazino[1',2':1,6]pyrido[3,4-b]indole-1,3-dione Examples 4a and 4b were prepared from indole as depicted in following Schemes 4 through 6. Threo isomer (+/−) Intermediate 13a and erythro isomer (+/−) Intermediate 13b were prepared from indole as shown in Scheme 4. The isolated threo isomer Intermediate 13a then was used to provide a mixture of cis and trans isomers at C6, which were separated as chloroacetyl isomers cis-(Intermediate 14a) and trans-(Intermediate 14b), as shown in Scheme 5. Each of these Intermediates 14a and 14b isomers then were used to provide the cis Example 4a and the trans Example 4b, respectively, as shown in Scheme 6.

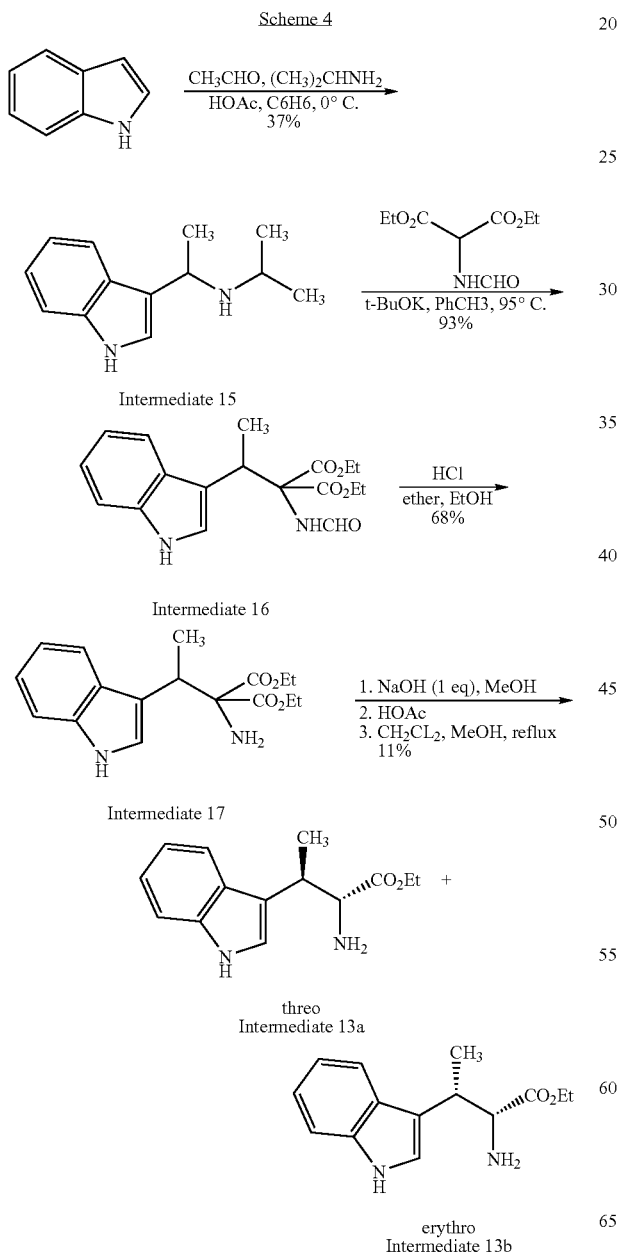

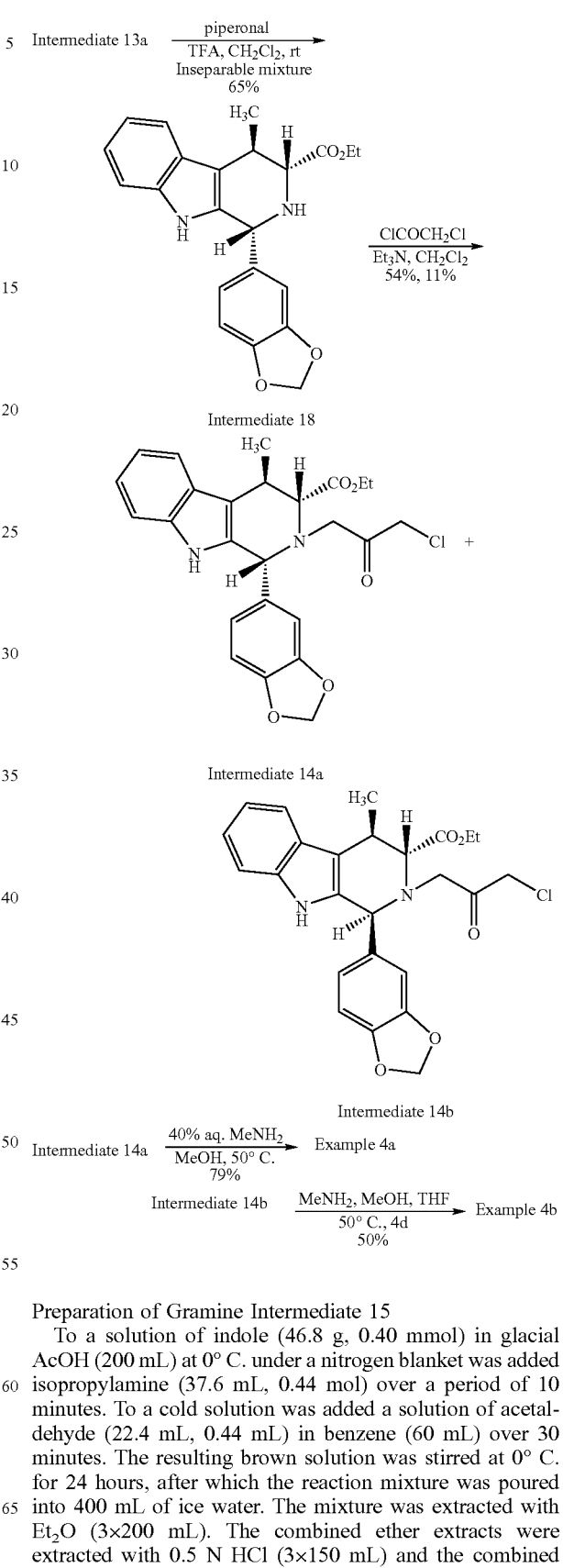

Preparation of Gramine Intermediate 15

To a solution of indole (46.8 g, 0.40 mmol) in glacial AcOH (200 mL) at 0° C. under a nitrogen blanket was added isopropylamine (37.6 mL, 0.44 mol) over a period of 10 minutes. To a cold solution was added a solution of acetaldehyde (22.4 mL, 0.44 mL) in benzene (60 mL) over 30 minutes. The resulting brown solution was stirred at 0° C. for 24 hours, after which the reaction mixture was poured into 400 mL of ice water. The mixture was extracted with $Et_2O$ (3×200 mL). The combined ether extracts were extracted with 0.5 N HCl (3×150 mL) and the combined aqueous extracts were washed with Et$_2$O (2×200 mL). The combined aqueous extracts were cooled to 0° C., then made basic with 50% aqueous NaOH to pH 12. The precipitate was extracted with CH$_2$Cl$_2$ (3×300 mL) and the combined extracts were washed with brine (200 mL), dried over Na$_2$SO$_4$, filtered, and the solvent was removed under reduced pressure to afford Intermediate 15 as a yellow semisolid (30 g, 37%): TLC R$_f$ (1:1 CH$_2$Cl$_2$/EtOAc)=0.11.

$^1$H NMR (300 MHz, CDCl$_3$) δ: 8.05 (br s, 1H), 7.70 (d, J=8.0 Hz, 1H), 7.37 (d, J=8.0 Hz, 1H), 7.25–7.05 (m, 3H), 4.34–4.23 (m, 1H), 2.87 (sep, J=7.0 Hz, 1H), 1.54 (d, J=7.6 Hz, 3H), 1.15–1.02 (m, 6H).

Preparation of N-Formylaminomalonate Intermediate 16

A mixture of Intermediate 15 (19.6 g, 99.7 mmol), diethyl N-formylaminomalonate (19.7 g, 99.7 mmol), and potassium tert-butoxide (1.09 g, 9.7 mmol) in toluene (250 mL) was heated at 90° C. under a nitrogen blanket for 3 days. The reaction mixture was cooled to room temperature and diluted with EtOAc (300 mL). The organic mixture was successively washed with 1 N HCl (3×150 mL) and brine (50 mL). The organic layer was dried over Na$_2$SO$_4$, filtered, and the solvent was removed under reduced pressure to afford Intermediate 16 as a brown foam-like solid which was suitable for use without further purification (32 g, 93%): TLC R$_f$ (1:1 CH$_2$Cl$_2$/EtOAc)=0.83.

$^1$H NMR (300 MHz, CDCl$_3$) δ: 8.26 (s, 1H), 8.20 (br s, 1H), 7.60 (d, J=8.0 Hz, 1H), 7.33 (d, J=8.0 Hz, 1H), 7.27–6.92 (m, 3H), 6.76 (s, 1H), 4.40–3.70 (m, 5H), 1.57 (d, J=6.5 Hz, 3H), 1.33–1.01 (m, 6H).

Preparation of Aminomalonate Intermediate 17

To a solution of Intermediate 16 (32 g, 92 mmol) in MeOH (500 mL) was added a solution of HCl (139 mL, 139 mmol, 1 N solution in Et$_2$O). The reaction mixture was kept at room temperature without stirring for 18 hours. Additional HCl solution (50 mL, 50 mmol, 1 N solution in Et$_2$O) was added, then the mixture was stirred at room temperature for an additional 22 hours. The solvent was removed under reduced pressure and the residue was diluted with water (500 mL). The mixture was extracted with EtOAc (3×250 mL), and the aqueous phase was neutralized with saturated NaHCO$_3$ solution to pH 8. The resulting mixture was extracted with CH$_2$Cl$_2$ (3×200 mL) and the combined organic extracts were concentrated under reduced pressure to provide Intermediate 17 as a brown oil which was suitable for use without further purification (20.5 g, 68%): TLC R$_f$ (10:1 CH$_2$Cl$_2$/EtOAc)=0.73.

$^1$H NMR (300 MHz, CDCl$_3$) δ: 8.22 (br s, 1H), 7.76 (d, J=7.6 Hz, 1H), 7.35–7.07 (m, 4H), 4.37–3.77 (m, 5H), 2.12 (br s, 2H), 1.46 (d, J=6.5 Hz, 3H), 1.30 (5, J=7.5 Hz, 3H), 1.06 (t, J=7.5 Hz, 3H).

Preparation of (+/−)-β-Methyltryptophan Intermediate 13a

To a solution of Intermediate 17 (20.4 g, 64 mmol) in MeOH (260 mL) and water (74 mL) was added a solution of NaOH (2.8 g, 7.0 mmol) in water (6 mL), and the mixture was stirred at room temperature for 18 hours. The resulting mixture was concentrated under reduced pressure (bath temperature 25° C.) and the residue was diluted with water (500 mL). The milky mixture was extracted with Et$_2$O (3×160 mL) to remove unreacted starting malonate. The aqueous layer was cooled in an ice bath and treated with AcOH until pH 4, then the resulting solution was concen trated under reduced pressure to a volume of 250 mL. The precipitate was filtered under reduced pressure to provide 6.0 g of a pink solid after drying in air for several hours. The solid was dissolved in a mixture of CH$_2$Cl$_2$/MeOH (2:1, 100 mL) The solution was heated at reflux for 2 hours to promote decarboxylation. The resulting solution was concentrated to a brown solid. This residue was purified by flash column chromatography, eluting with EtOAc, to provide threo isomer Intermediate 13a as a clear viscous oil (1.75, 11%): TLC R$_f$(EtOAc)=0.35.

$^1$H NMR (500 MHz, CDCl$_3$) δ: 8.15 (br s, 1H), 7.62 (d, J=7.6 Hz, 1H), 7.32 (d, J=7.6 Hz, 1H), 7.22–7.00 (m, 3H), 4.20–4.02 (m, 2H), 3.71–3.69 (m, 1H), 3.57–3.48 (m, 1H), 1.50–1.40 (m, 3H), 1.21–1.15 (m, 3H). The erthyro isomer Intermediate 13b was not isolated.

Preparation of β-Carboline Intermediate 18

Trifluoroacetic acid (0.62 mL, 8.11 mmol) was added to a mixture of Intermediate 13a (950 mg, 3.86 mmol) and piperonal (695 mg, 4.63 mmol) in CH$_2$Cl$_2$. (25 mL) at 0° C. under a nitrogen blanket, after which the mixture was warmed to room temperature stirred for 24 hours. The reaction mixture was diluted with CH$_2$Cl$_2$ (50 mL) and neutralized with saturated NaHCO$_3$ solution (10 mL). The organic layer was washed with water (10 mL) and brine (15 mL), dried over Na$_2$SO$_4$, filtered, and the solvent was removed under reduced pressure. The residue was purified by flash column chromatography, eluting with CH$_2$Cl$_2$/EtOAc (10:1), to afford β-carboline Intermediate 18 as an inseparable mixture of cis and trans isomers, and was used for the next step without further purification (950 mg, 65%): TLC R$_f$ (10:1 CH$_2$Cl$_2$/EtOAc)=0.40.

Preparation of cis-2-Chloroacetyl-β-carboline Intermediate 14a and trans-2-Chloroacetyl-β-carboline Intermediate 14b Chloroacetyl chloride (0.103 mL, 1.30 mmol) was added dropwise to a mixture of Intermediate 18 (379 mg, 1.0 mmol, inseparable mixture of cis and trans isomers) and Et$_3$N (0.182 mL, 1.3 mmol) in CH$_2$Cl$_2$ (10 mL) at 0° C. under a nitrogen blanket, and the resulting mixture was stirred at 0° C. for 2 hours, after which it was warmed to room temperature to stir for an additional 6 hours. The solution was diluted with CH$_2$Cl$_2$ (60 mL), washed with saturated NaHCO$_3$ solution (10 mL), water (10 mL), and brine (10 mL), then the solvent was removed under reduced pressure to provide a foam-like brown solid. The mixture was purified by flash column chromatography, eluting with CH$_2$Cl$_2$/EtOAc (30:1) to provide cis-2-chloroacetyl-β-carboline Intermediate 14a as a white solid (245 mg, 54%): TLC R$_f$ (30:1 CH$_2$Cl$_2$/EtOAc)=0.60.

$^1$H NMR (500 MHz, CDCl$_3$) δ: 7.67–7.51 (m, 2H), 7.30–7.10 (m, 2H), 6.90–6.60 (m, 4H), 5.91 (s, 2H), 4.56 (s, 1H), 4.35 (d, J=13.1 Hz, 1H), 4.24 (d, J=13.1 Hz, 1H), 4.10 (q, J=7.4 Hz, 2H), 3.97–3.80 (m, 1H), 3.51–3.37 (m, 1H), 1.44 (d, J=6.9 Hz, 3H), 1.0–0.85 (m, 3H); API MS m/z 455 [C$_{25}$H$_{27}$N$_2$O$_5$+H]$^+$.

The later eluting trans-2-chloroacetyl-β-carboline Intermediate 14b was obtained as a white solid (50 mg, 11%): TLC R$_f$ (30:1 CH$_2$Cl$_2$/EtOAc)=0.37.

$^1$H NMR (300 MHz, CDCl$_3$) δ: 7.60–7.49 (m, 2H), 7.27–7.08 (m, 3H), 7.00–6.92 (m, 1H), 6.87–6.75 (m, 2H), 6.02 (s, 1H), 5.97 (s, 1H), 5.92 (s, 1H), 4.20–3.75 (m, 6H), 1.67 (d, J=6.9 Hz, 3H), 1.20–1.10 (m, 3H); API MS m/z 455 [C$_{25}$H$_{27}$N$_2$O$_5$+H]$^+$.

PREPARATION OF EXAMPLE 4a

A mixture of Intermediate 14a (250 mg, 0.55 mmol) and $CH_3NH_2$ (0.28 mL, 4.4 mmol, 40% w/w solution in water) in $CH_3OH$ (18 mL) was heated at 45° C. under a nitrogen blanket for 3 days. Additional $CH_3NH_2$ (0.10 mL, 0.16 mmol, 40% w/w solution in water) was added to the reaction mixture and stirring was continued at 50° C. for an additional 18 hours. The resulting slurry was cooled to room temperature and filtered under reduced pressure. The solid was washed with MeOH (5×1 mL), then was dried in a vacuum oven at 70° C. for 1 day to provide Example 4a as a white solid (176 mg. 79%): mp 327–333° C.; TLC $R_f$ (4:1:05 $CH_2C_2$/EtOAc/MeOH)=0.83.

$^1$H NMR (300 MHz, DMSO-$d_6$) δ: 11.16 (s, 1H), 7.72 (d, J=7.9 Hz, 1H), 7.32 (d, J=7.9 Hz, 1H), 7.06 (t, J=6.9 Hz, 1H), 6.97 (t, J=6.9 Hz, 1H), 6.79 (d, J=8.0 Hz, 1H), 6.72 (d, J=1.5 Hz, 1H), 6.63 (dd, J=8.0, 1.6 Hz, 1H), 6.29 (s, 1H), 5.92 (s, 2H), 4.37 (d, J=16.6 Hz, 1H), 4.14 (d, J=10.1 Hz, 1H), 3.87 (d, J=16.6 Hz, 1H), 3.70–3.59 (m, 1H), 2.97 (s, 3H), 1.75 (d, J=6.3 Hz, 1H); API MS m/z 404 $[C_{23}H_{21}N_3O_4+H]^+$. Anal. Calcd. for $C_{23}H_{21}N_3O_4$: C, 68.47, H, 5.25; n, 10.42. Found: C, 68.31; H, 5.15; N, 10.30. The stereochemistry of Example 4a was confirmed to be the desired cis isomer by a series of NOE difference experiments: a positive NOE enhancement from the C12a proton at 4.14 ppm to the C6 proton at 6.29 ppm; a positive NOE enhancement from the C12a proton at 4.14 ppm to the C6 proton at 6.29 ppm; a positive NOE enhancement from the C6 proton at 6.29 ppm to the C12a proton at 4.14 ppm.

PREPARATION OF EXAMPLE 4b

A mixture of Intermediate 14b (146 mg. 0.32 mmol) and $CH_3NH_2$ (0.60 mL, 1.2 mmol, 2 N solution in THF) in MeOH (6 mL) was heated at 50° C. under a nitrogen blanket for 36 hours. The resulting mixture was concentrated under reduced pressure and the residue was stirred in EtOAc (2 mL) for 17 hours. The resulting slurry was filtered under reduced pressure, then the solid was washed with $CH_2Cl_2$ (5×2 mL) followed by a recrystallization from a small amount of $CHCl_3$/$CH_3CN$ (2:1) to provide Example 4b as a white solid (65 mg, 50%): mp 256–259° C.; TLC $R_f$(4:1:0.5 $CH_2Cl_2$/EtOAc/MeOH)=0.85.

$^1$H NMR (300 MHz, $CDCl_3$) δ: 7.95 (br s, 1H), 7.67 (d, J=7.7 Hz, 1H), 7.33 (d, J=7.7 Hz, 1H), 7.25–7.11 (m, 2H), 6.94 (s, 1H), 6.78–6.65 (m, 3H), 5.95 (s, 2H), 4.17 (d, J=17.7 Hz, 1H), 3.95 (d, J=17.7 Hz, 1H), 3.90 (d, J=8.9 Hz, 1H), 3.44–3.33 (m, 1H), 3.00 (s, 3H), 1.73 (d, J=6.7 Hz, 1H); API MS m/z 404 $[C_{23}H_{21}N_3O_4+H]^+$. Anal. Calcd. for $C_{23}H_{21}N_3O_4$.0.25$H_2O$: C. 67.72; H, 5.31; N, 10.30. Found: C, 68.04; H, 5.09; N, 10.34. The stereochemistry of Example 4b was confirmed to be the desired trans isomer by a series of NOE difference experiments: no NOE enhancement from the C12a proton at 3.90 ppm to the C6 proton at 6.94 ppm; no NOE enhancement from the C6 proton at 6.94 ppm to the C12a proton at 3.90 ppm.

EXAMPLE 5

(6S,12aR)-6-Benzo[1,3]dioxol-5-yl-6-hydroxy-2-methyl-2,3,6,7,12,12a-hexahydropyrzino[1',2':1,6]pyrido[3,4-b]indole-1,4-dione

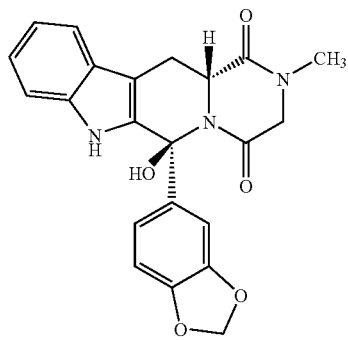

Example 5 was prepared from Intermediate 19 as illustrated below. Intermediate 19 was prepared as set forth in Daugan U.S. Pat. No. 5,859,006. Also, see M. Nakagawa et al., *Chem. Pharm. Bull.*, 37, p. 23 (1989).

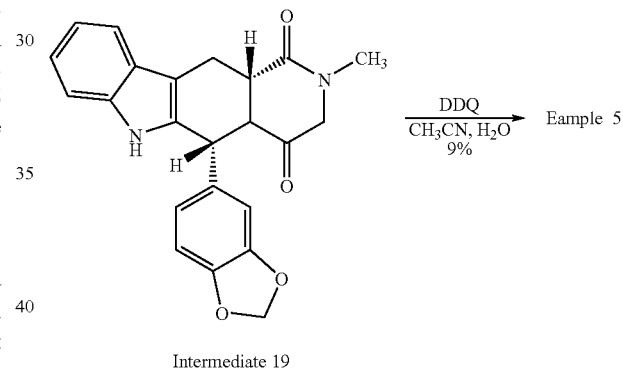

Intermediate 19

PREPARATION OF EXAMPLE 5

2,3-Dichloro-5,6-dicyano-1,4-benzoquinone (227 mg, 2.0 mmol) was added to a solution of Intermediate 19 (389 mg, 1.0 mmol) in a mixture of $CH_3CN$ (35 mL) and water (15 mL). The resulting dark brown solution was stirred at room temperature for 17 hours, followed by dilution with $CH_2Cl_2$ (125 mL) The organic layer was washed with saturated $NaHCO_3$ solution (3×20 mL), brine (20 mL), dried over $Na_2SO_4$, filtered, then the solvent was removed under reduced pressure. The resulting yellow solid was slurried in a small amount of MeOH, after which it was filtered under reduced pressure to afford the unreacted Intermediate 19 as a white solid (260 mg, 67% recovery). The filtrate was concentrated under reduced pressure and the residue was purified by flash column chromatography, eluting with $CH_2Cl_2$/EtOAc/MeOH (5:1:0.5), to afford Example 5 as an off-white solid (38 mg, 9%): mp 224–226° C.; TLC $R_f$ (5:1:05 $CH_2Cl_2$/EtOAc/MeOH)=0.54.

$^1$H NMR (300 MHz, $CDCl_3$) δ: 8.62 (bs, 1H), 7.72 (d, J=8.6 Hz, 1H), 7.41–7.34 (m, 3H), 7.31–7.18 (m, 2H), 6.90 (d, J=8.1 Hz, 1H), 6.76 (bs, 1H), 6.09 (s, 2H), 4.45–4.38 (m,

1H), 3.87 (dd, J=14.1, 5.6 Hz, 1H), 3.65 (dd, J=14.1, 5.6 Hz, 1H), 3.53 (d, J=17.4 Hz, 1H), 2.89 (d, J=17.4 Hz, 1H), 2.73 (s, 1H) ppm; CI MS m/z 406 $[C_{22}H_{19}N_3O_5+H]^+$; $[\alpha]_D^{25°}$ c.=+138.3 (c=0.125, CDCl$_3$). Anal. Calcd. for $C_{22}H_{19}N_3O_5$: C, 65.18; H, 4.72; N, 10.37. Found: C, 65.57; H, 4.70; N, 10.24. HPLC analysis (Aquasil C18 Column, 100×4.6 mm, Retention Time=8.0 min; 45:55/0.03 acetonitrile:water/TFA; flow=0.35 mL/min; detector @ 254 nm; temperature ambient) showed one peak, with a purity of 97.8%. The stereochemistry of Example 5 was confirmed to be the desired cis isomer by a series of NOE difference experiments: a positive NOE enhancement from the C12a proton at 4.41 ppm to the C6 hydroxyl proton at 6.76 ppm; a positive NOE enhancement from the C6 hydroxyl proton at 6.76 ppm to the C12a proton at 4.41 ppm.

Examples 6 and 7 were prepared in a manner similar to Examples 1–5.

Example 6

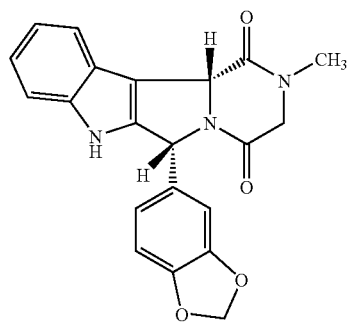

Example 7

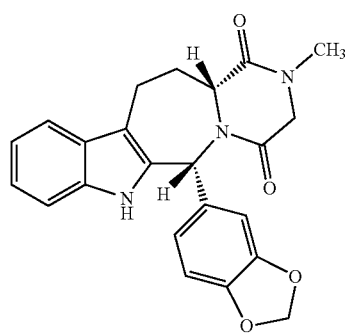

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the IC$_{50}$ value for the compound, i.e., the concentration of inhibitor required for 50% inhibition of enzyme activity. The IC$_{50}$ value for compounds of structural formula (I) were determined using recombinant human PDE5.

The compounds of the present invention typically exhibit an IC$_{50}$ value against recombinant human PDE5 of less than about 50 μM, and preferably less than about 25 μM, and more preferably less than about 15 μm. The compounds of the present invention typically exhibit an IC$_{50}$ value against recombinant human PDE5 of less than about 1 μM, and often less than about 0.05 μM. To achieve the full advantage of the present invention, a present PDE5 inhibitor has an IC., of about 0.1 nM to about 15 μM.

The production of recombinant human PDEs and the IC$_{50}$ determinations can be accomplished by well-known methods in the art. Exemplary methods are described as follows:

Expression of Human PDEs

Expression in *Saccharomyces Cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2–54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/ 3% glycerol. Approximately 24 hr later, cells were harvested, washed, and stored at −70° C.

Human Phosphodiesterase Preparations

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 μL reaction mixture containing (final concentrations) 40 mM iris HCl (pH 8.0), 1 μM ZnSO$_4$, 5 mM MgCl$_2$, and 0.1 mg/mL bovine serum albumin (BSA). PDE enzyme was present in quantities that yield <30% total hydrolysis of substrate (linear assay conditions). The assay was initiated by addition of substrate (1 mM [$^{32}$P]cAMP or cGMP), and the mixture was incubated for 12 minutes. Seventy-five (75) pg of *Crotalus atrox* venom then was added, and the incubation was continued for 3 minutes (15 minutes total). The reaction was stopped by addition of 200 μL of activated charcoal (25 mg/mL suspension in 0.1 M NaH$_2$PO$_4$, pH 4). After centrifugation. (750×g for 3 minutes) to sediment the charcoal, a sample of the supernatant was taken for radioactivity determination in a scintillation counter and the PDE activity was calculated.

Purification of PDE5 from *S. Cerevisiae*

Cell pellets (29 g) were thawed on ice with an equal volume of Lysis Buffer (25 mM Tris HCl, pH 8, 5 mM MgCl$_2$, 0.25 mM DTT, 1 mM benzamidine, and 10 μM ZnSO$_4$). Cells were lysed in a Microfluidizer® (Microfluidics Corp.) using nitrogen at 20,000 psi. The lysate was centrifuged and filtered through 0.45 μm disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM MgCl$_2$, 0.25 mM DTT, 10 μM ZnSO$_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM MgCl$_2$, 0.25 mM DTT, 10 µM ZnSO$_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 µM ZnSO$_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 µmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 µg/ml 5'-Nucleotidase, 1 mM EGTA, and 0.15 µM 8-[H$^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The IC$_{50}$ values for the compounds examined were determined from concentration-response curves typically using concentrations ranging from 10 nM to 10 µM. Tests against other PDE enzymes using standard methodology showed that compounds of the invention are selective for the cGMP-specific PDE enzyme.

Biological Data

The compounds according to the present invention were typically found to exhibit an IC$_{50}$ value of less than 500 nM (i.e., 0.5 µM). In vitro test data for representative compounds of the invention is given in the following table:

TABLE 1

In vitro Results

| Example | PDE5 IC$_{50}$ (µM) |
|---|---|
| 1 | 0.046 |
| 2a | 0.685 |
| 2b | 0.26 |
| 3 | 0.047 |
| 4a | 0.004 |
| 4b | 0.063 |
| 5 | 0.142 |

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

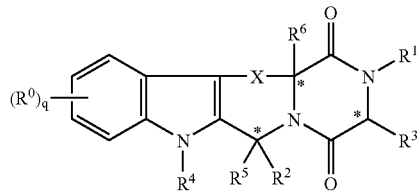

wherein R$^0$ is selected from the group consisting of halo and C$_{1-6}$alkyl;
R$^1$ is selected from the group consisting of hydro, C$_{1-6}$alkyl, C$_{2-6}$alkenyl, C$_{2-6}$alkynyl, haloC$_{1-6}$alkyl, C$_{3-8}$cycloalkyl, C$_{3-8}$cycloalkylC$_{1-3}$alkyl, arylC$_{1-3}$alkyl, and heteroarylC$_{1-3}$alkyl;
R$^2$ is selected from the group consisting of an optionally substituted monocyclic aromatic ring selected from the group consisting of benzene, thiophene, furan, and pyridine, and an optionally substituted bicyclic ring

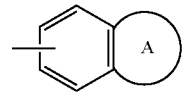

wherein the fused ring A is a 5- or 6-membered ring, saturated or partially or fully unsaturated, and comprises carbon atoms and optionally one or two heteroatoms selected from oxygen, sulfur, and nitrogen;
R$^3$ is selected from the group consisting of hydro and C$_{1-3}$alkyl, or R$^1$ and R$^3$ together represent a 3- or 4-membered alkyl or alkenyl chain component of a 5- or 6-membered ring;
R$^4$ is selected from the group consisting of hydro, C$_{1-6}$alkyl, C$_{3-8}$cycloalkyl, C$_{3-8}$heterocycloalkyl, C$_{2-6}$alkenyl, C$_{1-3}$alkylenearyl, arylC$_{1-3}$alkyl, C(=O)R$^a$, aryl, heteroaryl, C(=O)R$^a$, C(=O)NR$^a$R$^b$, C(=S)NR$^a$R$^b$, SO$_2$R$^a$, SO$_2$NR$^a$R$^b$, S(=O)R$^a$, S(=O)NR$^a$R$^b$, C(=O)NR$^a$C$_{1-4}$alkyleneOR$^a$, C(=O)NR$^a$C$_{1-4}$alkyleneHet, C(=O)C$_{1-4}$alkylenearyl, C(=O)C$_{1-4}$alkyleneheteroaryl, C$_{1-4}$alkylenearyl substituted with one or more of SO$_2$NR$^a$R$^b$, NR$^a$R$^b$, C(=O)OR$^a$, NR$^a$SO$_2$CF$_3$, CN, NO$_2$, C(=O)R$^a$, OR$^a$, C$_{1-4}$alkyleneNR$^a$R$^b$, and OC$_{1-4}$alkyleneNR$^a$R$^b$, C$_{1-4}$alkyleneheteroaryl, C$_{1-4}$alkyleneHet, C$_{1-4}$alkyleneC(=O)C$_{1-4}$alkylenearyl, C$_{1-4}$alkyleneC(=O)C$_{1-4}$ alkyleneheteroaryl, C$_{1-4}$alkyleneC(=O)Het, C$_{1-4}$alkyleneC(=O)NR$^a$R$^b$, C$_{1-4}$alkyleneOR$^a$, C$_{1-4}$alkyleneNR$^a$C(=O)R$^a$, C$_{1-4}$alkyleneOC$_{1-4}$alkyleneOR$^a$, C$_{1-4}$alkyleneNR$^a$R$^b$, C$_{1-4}$alkyleneC(=O)OR$^a$, and C$_{1-4}$alkyleneOC$_{1-4}$alkyleneC(=O)OR$^a$;
R$^5$ is selected from the group consisting of hydro, OR$^a$, C$_{1-6}$alkyl, aryl, heteroaryl, arylC$_{1-3}$alkyl, C$_{1-3}$alkylenearyl, C$_{1-3}$alkyleneHet, C$_{3-8}$cycloalkyl, and C$_{3-8}$heterocycloalkyl;
R$^6$ is selected from the group consisting of hydro, C$_{1-6}$alkyl, C$_{3-8}$cycloalkyl, C$_{3-8}$heterocycloalkyl, aryl, heteroaryl, OR$^a$, C(=O)OR$^a$, C(=O)R$^a$, C(=O)NR$^a$R$^b$, C(=S)OR$^a$, and C(=S)NR$^a$R$^b$;
X is selected from the group consisting of CHR$^7$, CHR$^7$CH$_2$, CH$_2$CHR$^7$, CR$^7$=CH, CH=CR$^7$, QCHR$^7$, and CHR$^7$Q, or X is a bond;

Q is O, S, or NR$^a$;

R$^7$ is selected from the group consisting of hydro, OR$^a$, C$_{1-6}$alkyl, C$_{1-3}$cycloalkyl, C$_{3-8}$heterocycloalkyl, aryl, heteroaryl, C$_{1-3}$alkylenearyl, C$_{1-3}$alkyleneheteroaryl, C$_{1-3}$alkyleneHet, arylC$_{1-3}$alkyl, and heteroarylC$_{1-3}$alkyl;

Het represents a 5- or 6-membered heterocyclic ring, saturated or partially or fully unsaturated, containing at least one heteroatom selected from the group consisting of oxygen, nitrogen, and sulfur, and optionally substituted with C$_{0-4}$alkyl or C(=O)OR$^a$;

R$^a$ is selected from the group consisting of hydro, C$_{1-6}$alkyl, aryl, arylC$_{1-3}$alkyl, C$_{1-3}$alkylenearyl, heteroaryl, heteroarylC$_{1-3}$alkyl, and C$_{1-3}$alkyleneheteroaryl;

R$^b$ is selected from the group consisting of hydro, C$_{1-6}$alkyl, aryl, heteroaryl, arylC$_{1-3}$alkyl, heteroarylC$_{1-3}$ alkyl, C$_{1-3}$alkyleneN(R$^a$)$_2$, C$_{1-3}$alkylenearyl, C$_{1-3}$alkyleneHet, haloC$_{1-3}$alkyl, C$_{3-8}$cycloalkyl, C$_{3-8}$heterocycloalkyl, C$_{1-3}$alkyleneheteroaryl, C$_{1-3}$alkyleneC(=O)OR$^a$, and C$_{1-3}$alkyleneC$_{3-8}$heterocycloalkyl;

or R$^a$ and R$^b$ are taken together to form a 5- or 6-membered ring, optionally containing at least one heteroatom;

q is 0, 1, 2, 3, or 4;

with the proviso that if X is CHR$^7$, at least one of R$^4$, R$^5$, R$^6$, and R$^7$ is different from hydrogen; and or a pharmaceutically acceptable salt or hydrates thereof.

2. The compound of claim 1 represented by the formula

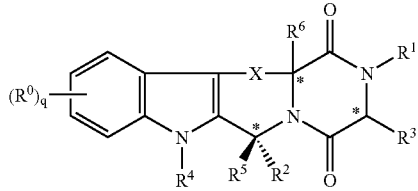

or pharmaceutically acceptable salt or hydrates thereof.

3. The compound of claim 1 wherein q is 0.

4. The compound of claim 1 wherein R$^1$ is selected from the group consisting of C$_{1-6}$alkyl, C$_{3-8}$cycloalkyl, C$_{2-6}$alkenyl, and haloC$_{1-6}$alkyl.

5. The compound of claim 1 wherein R$^3$ is hydro.

6. The compound of claim 1 wherein R$^1$ and R$^3$ together represent a 3- or 4-membered alkyl chain component.

7. The compound of claim 1 wherein R$^2$ is the optionally substituted bicyclic ring system

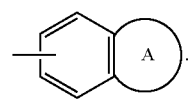

8. The compound of claim 7 wherein R$^2$ is

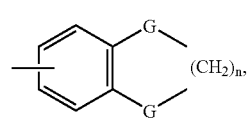

and wherein n is an integer 1 or 2, and G, independently, are C(R$^a$)$_2$, O, S, or NR$^a$.

9. The compound of claim 1 wherein R$^2$ is selected from the group consisting of

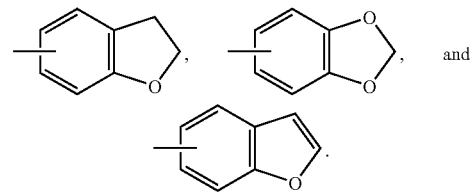

10. The compound of claim 1 wherein R$^4$ is selected from the group consisting of hydro, aryl, heteroaryl, C$_{1-4}$alkyleneHet, C$_{1-4}$-alkyleneheteroaryl, C$_{1-4}$alkylenearyl, C$_{1-4}$alkyleneC(=O)C$_{1-4}$alkylenearyl, C$_{1-4}$alkyleneC(=O)OR$^a$, C$_{1-4}$alkyleneC(=O)NR$^a$R$^b$, C$_{1-4}$alkyleneC(=O)Het, C$_{1-4}$alkyleneNR$^a$R$^b$, C$_{1-4}$alkyleneNR$^a$C(=O)R$^a$, and C$_{1-4}$alkyleneOC$_{1-4}$alkyleneOR$^a$.

11. The compound of claim 10 wherein R$^a$ is selected from the group consisting of hydrogen, C$_{1-4}$ alkyleneheteroaryl, wherein the heteroaryl group is selected from the group consisting of benzimidazole, a triazole, and imidazole; C$_{1-4}$alkyleneHet, wherein Het is selected from the group consisting of piperazinyl, morpholinyl, pyrrolidinyl, pyrrolidonyl, tetrahydrofuranyl, piperidinyl,

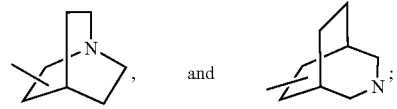

C$_{1-4}$alkyleneC$_6$H$_5$, optionally substituted with one to three groups selected from the group consisting of C(=O)OR$^a$, NR$^a$R$^b$, NR$^a$SO$_2$CF$_3$, SO$_2$NR$^a$R$^b$, CN, OR$^a$, C(=O)R$^a$, C$_{1-4}$alkyleneNR$^a$R$^b$, nitro, OC$_{1-4}$alkylenearyl, and OC$_{1-4}$alkyleneNR$^a$R$^b$; C$_{1-4}$alkyleneC(=O)benzyl; C$_{1-4}$alkyleneC(=O)OR$^a$, C$_{1-4}$alkyleneC(=O)NR$^a$R$^b$; C$_{1-4}$alkyleneC(=O)NR$^a$R$^c$; OC$_{1-4}$alkyl; C$_6$H$_5$; C$_{1-4}$alkyleneNR$^a$R$^b$; C$_{1-4}$alkyleneOR$^a$, C$_{1-4}$alkyleneNHC(=O)R$^a$; and C$_{1-4}$alkyleneOC$_{1-4}$alkyleneOR$^a$.

12. The compound of claim 1 wherein R$^5$ is selected from the group consisting of hydro, OR$^a$, C$_{1-6}$alkyl, aryl, and heteroaryl.

13. The compound of claim 1 wherein R$^6$ is selected from the group consisting of hydro, OR$^a$, C$_{1-6}$alkyl, C$_{3-8}$cycloalkyl, C$_{3-8}$heterocycloalkyl, aryl, and heteroaryl.

14. The compound of claim 1 wherein X is a bond, or X is selected from the group consisting of CHR$^7$, CHR$^7$CH$_2$, CH$_2$CHR$^7$, CH=CR$^7$, and CR$^7$=CH.

15. The compound of claim 14 wherein R$^7$ is selected from the group consisting of hydro, OR$^a$, C$_{1-6}$alkyl, aryl, heteroaryl, C$_{3-8}$cycloalkyl, and C$_{1-8}$heterocycloalkyl.

16. The compound of claim 1 wherein X is a bond, or X is selected from the group consisting of CH$_2$, CH$_2$CH(C$_6$H$_5$), CH$_2$CH(CH$_3$), CH$_2$CH$_2$, and CH(OH).

17. The compound of claim 1 wherein q is 0, or $R^0$ is selected from the group consisting of halo and methyl; $R^1$ is methyl; $R^2$ is selected from the group consisting of

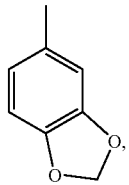 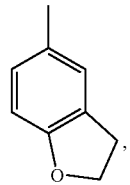 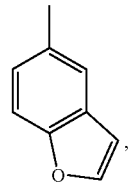

$R^4$ is selected from the group consisting of hydrogen and $C_{1-6}$ alkyl; $R^5$ is selected from the group consisting of H, $CH_3$, and OH; $R^6$ is selected from the group consisting of hydro, methyl, OH, phenyl, and cyclohexyl; and X is selected from the group consisting of $CHR^7$ and $CHR^7CH_2$, or X is a bond; and $R^7$ is selected from the group consisting of hydro, OH, methyl, and phenyl.

18. The compound of claim 1 wherein q is 0, $R^1$ is methyl, $R^3$ is hydrogen, $R^4$ is hydrogen, $R^5$ is hydro or methyl, and $R^6$ is hydrogen or methyl.

19. The compound of claim 18 wherein $R^2$ is selected from the group consisting of

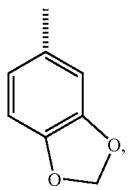 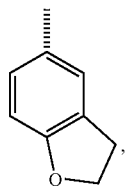 and 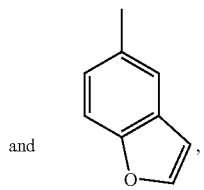

20. A compound selected from the group consisting of
(6R,12aR)-6-benzo[1,3]dioxol-5-yl-2,12a-dimethyl-2,3, 6,7,12,12a-hexahydro-pyrazino-[1',2':1,6]pyrido-[3,4-b]indole-1,4-dione;
(+−, cis-6-benzo[1,3]dioxol-5-yl-2,6-dimethyl-2,3,6,7, 12,12a-hexahydropyrazino[1',2':1,6]pyrido-[3,4-b]indole-1,4-dione;
(+−, cis, trans methyl)-6-benzo[1,3]dioxol-5-yl-2,12-dimethyl-2,3,6,7,12,12a-hexahydropyrazino-[1',2':1,6]pyrido[3,4-b]indole-1,3-dione;
(+−, trans, trans methyl)-6-benzo[1,3]dioxol-5-yl-2,12-dimethyl-2,3,6,7,12,12a-hexahydropyrazino-[1',2':1,6] pyrido[3,4-b]indole-1,3-dione;
(+−, 6,12a cis-12,12a-trans)-6-benzo-(1,3)-dioxol-5-yl-methyl-12-phenyl-2,3,6,7,12,12a-hexahydropyrazino-[1',2':1,6]pyrido[3,4-b]indole-1,4-dione;
(+−, trans)-6-benzo[1,3]dioxol-5-yl-2,6-dimethyl-2,3,6,7, 12,12a-hexahydropyrazino[1',2':1,6]pyrido-[3,4-b]indole-1,4-dione; and
(6S,12aR)-6-benzo[1,3]dioxol-5-yl-6-hydroxy-2-methyl-2,3,6,7,12,12a-hexahydropyrzino[1',21:1,6]pyrido[3,4-b]indole-1,4-dione;
or a pharmaceutically acceptable salt and solvates thereof.

21. A compound of claim 1 having the formula:

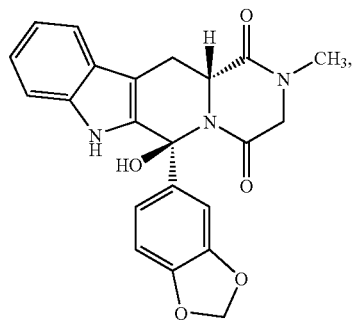

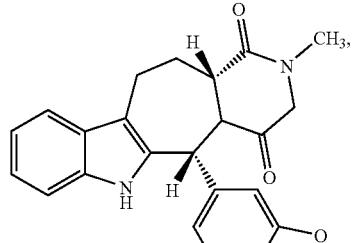

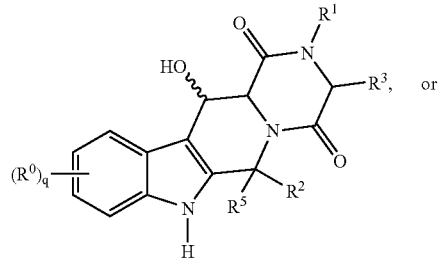

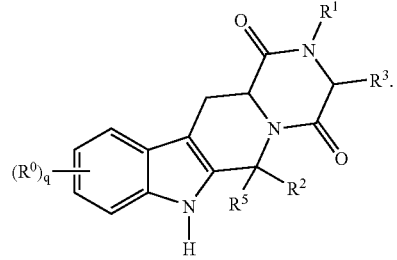

22. A pharmaceutical composition comprising a compound of claim 1, together with a pharmaceutically acceptable diluent or carrier.

23. A method of treating a male animal for male erectile dysfunction comprising treating said male animal with an effective amount of a pharmaceutical composition comprising a compound of claim 1, together with a pharmaceutically acceptable diluent or carrier.

24. The method of claim 23 wherein the treament is an oral treatment.

25. A method of treating a female animal for female arousal disorder, comprising administration of an effective dose of a compound of claim 1, or a pharmaceutically acceptable salt of hydrate thereof, to the female animal.

26. The method of claim 25 wherein the treatment is an oral treatment.

* * * * *

UNITED STATES PATENT AND TRADEMARK OFFICE
CERTIFICATE OF CORRECTION

PATENT NO. : 7,105,506 B2
APPLICATION NO. : 10/479352
DATED : September 12, 2006
INVENTOR(S) : Mark W. Orme et al.

It is certified that error appears in the above-identified patent and that said Letters Patent is hereby corrected as shown below:

On the First Page:

At line (54), "PDE5-INHIBITORS" should be -- PDE5 INHIBITORS --.

At line (73), "Icos" should be -- ICOS --.

In the Specification:

At Column 1, line 2, "PDE5-INHIBITORS" should be -- PDE5 INHIBITORS --.

At Column 1, line 43, "aryl-C" should be -- arylC --.

At Column 1, line 66, "$C_{3-8}$-heterocycloalkyl" should be -- $C_{3-8}$heterocycloalkyl --.

At Column 2, line 10, "$C_{1-4}$-alkyleneC" should be -- $C_{1-4}$alkyleneC --.

At Column 2, line 41, "$C_{1-3}$-alkylene" should be -- $C_{1-3}$alkylene --.

At Column 5, line 27, "(=O)-$NR^aR^c$" should be -- (=O)$NR^aR^c$ --.

At Column 5, line 28, "alkylene-$OR^a$" should be -- alkylene$OR^a$ --.

At Column 6, lines 56-57, please close up the paragraph break.

At Column 9, line 40, "pyrogen-,free" should be -- pyrogen-free --.

At Column 12, line 20, "$NH_2$" should be -- NH --.

At Column 13, line 8, "→" should be to the left of Compound VIII.

At Column 13, line 58, " $\xrightarrow[POCl_3]{P_2O_5}$ " should be to the left of Compound XI.

At Column 17, line 4, "1,2'" should be -- 1',2' --.

At Column 18, line 23, "3H)" should be -- 3H). --.

UNITED STATES PATENT AND TRADEMARK OFFICE
CERTIFICATE OF CORRECTION

PATENT NO. : 7,105,506 B2
APPLICATION NO. : 10/479352
DATED : September 12, 2006
INVENTOR(S) : Mark W. Orme et al.

It is certified that error appears in the above-identified patent and that said Letters Patent is hereby corrected as shown below:

At Column 20, line 20, " 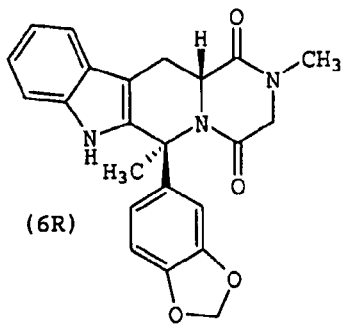 " should be

-- 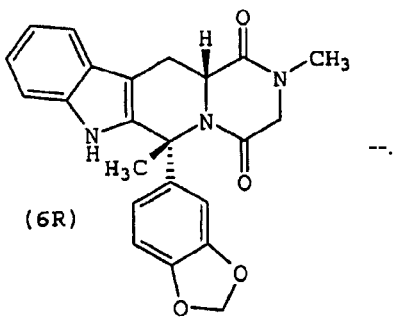 --.

At Column 21, line 5, "addition" should be -- additional --.

At Column 21, line 9, "$Na_2SO_{41}$" should be -- $Na_2SO_4$,--.

At Column 21, line 21, "$^1H$" should start a new paragraph.

At Column 21, line 58, "3230°" should be -- 323° --.

At Column 22, line 20, "(780)mg)" should be -- (780 mg) --.

At Column 22, line 44, "$O_4.0.75$" should be -- $O_4·0.75$ --.

At Column 24, line 66, "cooled to in" should be -- cooled in --.

At Column 26, line 19, please add -- Intermediate 11 --.

UNITED STATES PATENT AND TRADEMARK OFFICE
CERTIFICATE OF CORRECTION

PATENT NO. : 7,105,506 B2
APPLICATION NO. : 10/479352
DATED : September 12, 2006
INVENTOR(S) : Mark W. Orme et al.

It is certified that error appears in the above-identified patent and that said Letters Patent is hereby corrected as shown below:

At Column 26, line 22, " 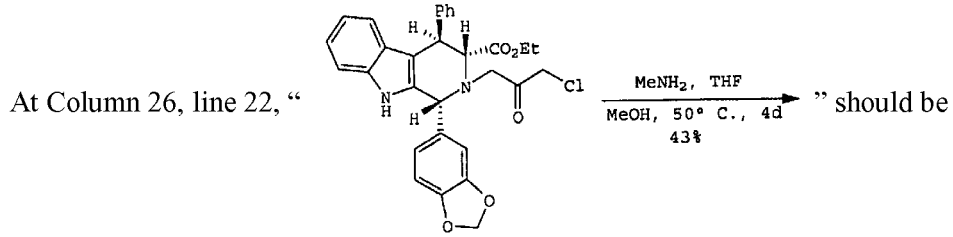 " should be

-- 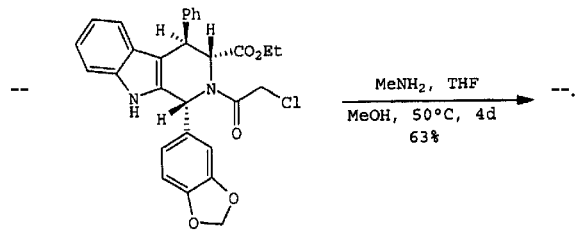 --.

At Column 26, line 23, "43%" should be -- 63% --.

At Column 27, line 32, "while" should be -- white --.

At Column 27, lines 66-67, "vacuum-filtration" should be -- vacuum filtration --.

At Column 29, line 23, "C6H6" should be -- $C_6H_6$ --.

At Column 29, line 30, "PhCH3" should be -- $PhCH_3$ --.

At Column 29, line 46, "CH2CL2" should be -- $CH_2Cl_2$ --.

UNITED STATES PATENT AND TRADEMARK OFFICE
CERTIFICATE OF CORRECTION

PATENT NO.       : 7,105,506 B2                                   Page 4 of 7
APPLICATION NO.  : 10/479352
DATED            : September 12, 2006
INVENTOR(S)      : Mark W. Orme et al.

It is certified that error appears in the above-identified patent and that said Letters Patent is hereby corrected as shown below:

At Column 30, line 40, " 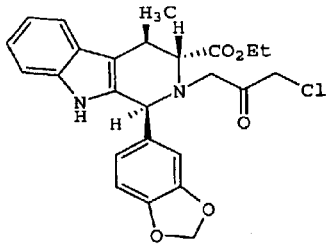 " should be

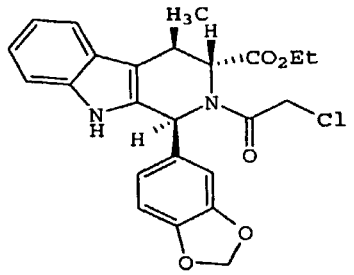

-- --.

At Column 31, line 67, "concen" should be -- concen- --.

At Column 33, line 15, "$CH_2C_2$" should be -- $CH_2Cl_2$ --.

At Column 33, line 26, "n," should be -- N, --.

At Column 33, line 60, "$O_4.0.25$" should be -- $O_4 \cdot 0.25$ --.

At Column 33, line 60, "C." should be -- C, --.

UNITED STATES PATENT AND TRADEMARK OFFICE
CERTIFICATE OF CORRECTION

PATENT NO. : 7,105,506 B2
APPLICATION NO. : 10/479352
DATED : September 12, 2006
INVENTOR(S) : Mark W. Orme et al.

It is certified that error appears in the above-identified patent and that said Letters Patent is hereby corrected as shown below:

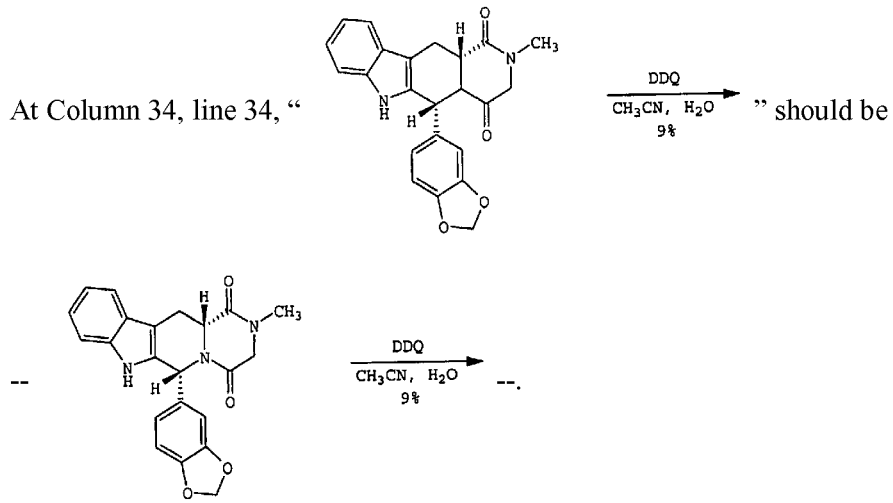

At Column 34, line 34, " " should be -- --.

At Column 34, line 34, "Eample 5" should be -- Example 5 --.

At Column 34, line 53, "(125 mL)" should be -- (125 mL). --.

At Column 34, line 64, "5:1:05" should be -- 5:1:0.5 --.

At Column 36, line 2, "IC.," should be -- $IC_{50}$ --.

At Column 36, line 42, "iris HCl" should be -- Tris HCl --.

At Column 36, line 47, "$^{32}$P" should be -- 32P --.

At Column 36, line 48, "pg" should be -- µg --.

At Column 39, line 3, "$C_{1-3}$cycloalkyl" should be -- $C_{3-8}$cycloalkyl --.

At Column 39, line 11, "$C_{0-4}$alkyl" should be -- $C_{1-4}$alkyl --.

At Column 39, line 28, "hydrogen; and" should be -- hydrogen; --.

At Column 39, line 29, "hydrates" should be -- hydrate --.

UNITED STATES PATENT AND TRADEMARK OFFICE
CERTIFICATE OF CORRECTION

PATENT NO. : 7,105,506 B2
APPLICATION NO. : 10/479352
DATED : September 12, 2006
INVENTOR(S) : Mark W. Orme et al.

It is certified that error appears in the above-identified patent and that said Letters Patent is hereby corrected as shown below:

At Column 39, line 42, "hydrates" should be -- hydrate --.

At Column 39, line 44, "$R^1$" should be -- $R^2$ --.

At Column 40, line 18, "$C_{1-4}$-alkyleneheteroaryl" should be -- $C_{1-4}$alkyleneheteroaryl --.

At Column 40, line 24, "$R^a$" should be -- $R^4$ --.

At Column 40, line 48, "$C_{1-4}$alkyleneOC" should be -- $C_{2-4}$alkyleneOC --.

At Column 40, line 64, "$C_{1-8}$heterocycloalkyl" should be -- $C_{3-8}$heterocycloalkyl --.

At Column 41, line 61, "hexahydropyrzino[1',21:1,6]" should be -- hexahydropyrazino[1',2':1,6] --.

At Column 41, line 63, "salt and solvates" should be -- salt or hydrate --.

At Column 42, line 20, " 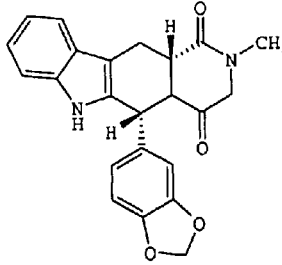 " should be

-- 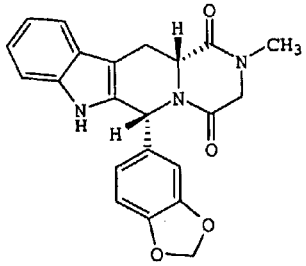 --.

UNITED STATES PATENT AND TRADEMARK OFFICE
CERTIFICATE OF CORRECTION

PATENT NO. : 7,105,506 B2
APPLICATION NO. : 10/479352
DATED : September 12, 2006
INVENTOR(S) : Mark W. Orme et al.

It is certified that error appears in the above-identified patent and that said Letters Patent is hereby corrected as shown below:

At Column 42, lines 55-56, "treatment is an oral treatment" should be -- pharmaceutical composition is orally administered --.

At Column 42, line 60, "salt of hydrate" should be -- salt or hydrate --.

At Column 42, lines 61-62, "treatment is an oral treatment" should be -- pharmaceutical composition is orally administered --.

Signed and Sealed this

Tenth Day of June, 2008

JON W. DUDAS
*Director of the United States Patent and Trademark Office*